United States Patent [19]

Boguslaski et al.

[11] 4,380,580

[45] Apr. 19, 1983

[54] HETEROGENOUS CHEMILUMINESCENT SPECIFIC BINDING ASSAY

[75] Inventors: Robert C. Boguslaski, Elkhart; Robert J. Carrico, Bremen, both of Ind.; James E. Christner, Ann Arbor, Mich.

[73] Assignee: Miles Laboratories, Inc., Elkhart, Ind.

[21] Appl. No.: 50,681

[22] Filed: Jun. 21, 1979

Related U.S. Application Data

[60] Division of Ser. No. 894,838, Apr. 10, 1978, which is a continuation of Ser. No. 667,982, Mar. 18, 1976, abandoned, which is a continuation-in-part of Ser. No. 572,008, Apr. 28, 1975, abandoned.

[51] Int. Cl.$^3$ .................... G01N 33/54; G01N 33/58; G01N 21/76
[52] U.S. Cl. ........................................ 435/7; 436/500; 436/518; 436/532; 436/805; 436/817; 436/818; 422/61
[58] Field of Search ..................... 23/230 B; 424/8, 12; 252/408; 435/7; 436/518

[56] References Cited

U.S. PATENT DOCUMENTS

| | | | |
|---|---|---|---|
| 4,011,219 | 3/1977 | Nishii | 260/250 P |
| 4,104,029 | 8/1978 | Maier | 23/230 B |
| 4,181,650 | 1/1980 | Maier | 424/12 X |

*Primary Examiner*—Sidney Marantz
*Attorney, Agent, or Firm*—Andrew L. Klawitter

[57] ABSTRACT

A heterogeneous specific binding assay which employs a substance having reactant activity, i.e., a reactant, in a chemiluminescent reaction as a labeling substance in the detection of a ligand in a liquid medium. The method is carried out using reagent means which comprises, as its labeled constituent, a conjugate formed of a specific binding substance coupled to the chemiluminescent reactant. The activity of the conjugated reactant in the chemiluminescent reaction, i.e., the production of light, is utilized as means for monitoring the extent of binding of the labeled constituent in conventional heterogeneous specific binding assay schemes. The presence of a ligand in a liquid medium may be determined following conventional competitive binding manipulative techniques. After the necessary separation of the bound- and free-phases resulting in the specific binding reaction system, the extent of binding of the labeled constituent is determined by contacting either phase with the necessary materials to form the chemiluminescent monitoring reaction and measuring the light produced.

56 Claims, No Drawings

HETEROGENOUS CHEMILUMINESCENT SPECIFIC BINDING ASSAY

CROSS-REFERENCE TO RELATED APPLICATION

This is a division of application Ser. No. 894,838, filed Apr. 10, 1978, which is a continuation of application Ser. No. 667,982, filed Mar. 18, 1976, now abandoned, which is a continuation-in-part of application Ser. No. 572,008, filed Apr. 28, 1975, now abandoned.

BACKGROUND OF THE INVENTION

1. Field of the Invention

This invention relates to methods and means for determining the presence of a ligand in a liquid medium based on the affinity of the ligand for a specific binding partner thereof. In particular, this invention relates to methods and means for use in specific binding assays which do not employ radioactive materials or modified enzymes as the labeling substance.

The desirability of a convenient, reliable, and non-hazardous means for detecting the presence of low concentrations of substances in liquids is self-evident. This is particularly true in the field of clinical chemistry where constituents of body fluids which may appear in concentrations as low as $10^{-11}$ molar are known to be of pathological significance. The difficulty of detecting such low concentrations is compounded in the field of clinical chemistry where sample size is usually quite limited.

Classically, substances have been detected in liquids based on a reaction scheme wherein the substance to be detected is a necessary reactant. The presence of unknown is indicated by the appearance of a reaction product or the disappearance of a known reactant. In certain instances, such as assay method may be quantitative, based on a meaurement of either the rate of appearance of product or disappearance of reactant or measurement of the aggregate amount of product produced or reactant consumed in attaining equilibrium. Each assay reaction system is necessarily either limited to use in the detection of only a small group of substances or is non-specific.

2. Description of the Prior Art

The search for assay systems which are highly specific yet adaptable to the detection of a wide range of substances has evolved the radioimmunoassay. In this system a known amount of a radiolabeled form of the substance to be detected is allowed to compete with the unknown for a limited quantity of antibody specific for the unknown. The amount of the labeled form that becomes bound to antibody varies inversely with the level of unknown present. Inherent in the radioimmunoassay technique is the need to separate the labeled form of substance to be detected which becomes bound to antibody, the bound-phase, from that which does not become so bound, the free-phase. While various ways of accomplishing the required separation have been developed, as exemplified in U.S. Pat. Nos. 3,505,019; 3,555,143; 3,646,346; 3,720,760; and 3,793,445, all require at least one separate manipulative step, such as filtering, centrifuging, washing, or draining a column to insure efficient separation of the bound and free phases. Such separation is often accomplished by forming a system comprised of an insoluble portion containing the bound-phase and a liquid portion containing the free-phase such that the amount of radioactive label in either portion is a function of the extent of binding of the labeled material, and thus a function of the amount of ligand in the sample tested. The term "heterogeneous" as generally used by the scientific community and as applied herein, means those specific binding assays wherein a separation of the bound- and free-phases is accomplished. Such a separation is necessary to carry out a specific binding assay where the labeled material in the bound-phase is indistinguishable from that in the free-phase.

Because of the hazard and difficulty of handling radioactive materials, there have been many attempts to devise convenient specific binding assay systems which are as sensitive and rapid as radioimmunoassays but which utilize features other than radioactivity as the means for monitoring the binding reaction. As will be discussed more fully hereinafter, materials which have been utilized as the labeling substance in place of radioactive atoms or molecules include such diverse materials as enzymes, fluorescent molecules, and bacteriophages.

Exemplary of methods which have been developed using an enzyme as the labeling substance are those described in U.S. Pat. Nos. 3,654,090; 3,791,932; 3,839,153; 3,850,752; and 3,879,262 and in the *Journal of Immunological Methods* 1: 247(1972) and the *Journal of Immunology* 109:129(1972). In each of the described methods an enzyme is chemically coupled to either the ligand to be detected or a binding partner thereof and an appropriate heterogeneous specific binding reaction scheme is constructed whereby after incubation with a sample, the amount of enzymatic activity associated with either the insoluble portion or the liquid portion is a function of the amount of ligand in the sample. The problems associated with the synthesis and characterization of the enzyme-conjugates are serious short comings of this approach.

Of interest is the enzyme-tagged immunoassay described in U.S. Pat. No. 3,817,837. This method does not require the use of a partitioned (i.e. insoluble portion/liquid portion) specific binding reaction system and the separation procedure necessitated thereby since the enzyme-tagged ligand is designed such that upon reaction with the binding partner of the ligand, enzymatic activity is inhibited. Thus, the ratio of bound tagged material to that in free form can be determined by monitoring changes in enzymatic activity. Nonetheless, this method suffers from the difficulty of preparing well-characterized enzyme-tagged conjugates and of finding enzymes that will fit the basic design of the system.

British Pat. No. 1,392,403 and French Pat. No. 2,201,299, which patents correspond to U.S. Pat. No. 3,880,934, describe a specific binding assay which utilizes a non-active precursor of a spectrophotometrically-active substance as the labeling substance. After incubation of the sample with the specific binding reaction system, the insoluble and liquid portions are separated and the amount of labeling substance present in the liquid portion, which is a function of the amount of ligand to be detected in the sample, is determined by carrying out reaction steps that transform the inactive labeling substance into a chromogen or fluorometrically active material which is then measured by conventional means.

Other specific binding assay methods employing different types of labeling substances are disclosed in: U.S.

Pat. No. 3,850,578 which discloses the use of electron spin resonance as a labeling means; U.S. Pat. No. 3,901,654 which discloses the use of fluorescence quenching and enhancement as a labeling means; and Report No. PB-224,875 of the National Technical Information Service (NTIS) of the U.S. Department of Commerce (1973) which describes an unsuccessful attempt to use hemin chloride as a labeling substance in a heterogeneous assay system monitored by a chemiluminescence reaction. *Nature* 219:186(1968) describes in great detail certain radioimmunoassay procedures and makes a passing reference of a very general nature to the possible use of coenzymes and viruses in place of radioisotopes as labeling substances. However, the author provides no enlightenment as to how to carry out an assay using such alternative labeling substances, or in fact as to whether such an assay would be operable. For further background, reference may be had to *Principles of Competitive Protein-Binding Assays*, ed. Odell and Daughaday (J. B. Lippincott Co., Philadelphia, 1972) which discusses in breadth the various known assay schemes and the different materials and features that have been used as labels for specific binding assays.

Even though many new types of specific binding assays have been suggested and investigated, the radioimmunoassay and the various enzyme-tagged immunoassays remain the most widely used and improved. However, both types of systems have obvious shortcomings, the radioimmunoassay in its use of radioactive material which is hazardous and requires careful handling and the enzyme-tagged immunoassays in the difficulty of preparing useful enzyme-tagged conjugates.

It is therefore an object of the present invention to provide a novel method and means for detecting a ligand in a liquid which do not employ inconvenient radioactive materials or modified enzymes as the labeling substance.

Further, it is an object of the present invention to provide a heterogeneous specific binding assay method and means which are more versatile and convenient than those of the prior art.

Another object of the present invention is to provide a heterogeneous specific binding assay method and means which employ a labeling substance which is capable of being coupled to the ligand or to a specific binding partner thereof more conveniently than can the enzyme of the prior art method.

It is also an object of the present invention to provide a heterogeneous specific binding assay method and means which employ a conjugate comprising a labeling substance which is more conveniently detectable using a wide variety of sensitive monitoring reaction systems than is the enzyme in the prior art method.

SUMMARY OF THE INVENTION

The present invention provides a highly convenient, versatile, and sensitive improved heterogeneous specific binding assay method and means based on the use of, as labeling substance, a substance which exhibits reactant activity as a constituent of a predetermined reaction system, such substance being referred to herein as the reactant. The inventive labeling substance may be used in any of the conventional heterogeneous specific binding assay schemes. The amount of the reactant present in either of the bound- and free-phases is determined by contacting either phase with at least one reagent which forms, with the reactant, the predetermined reaction system which serves as means for monitoring the specific binding reaction. Quantitative determinations are carried out by comparing the amount of reactant activity measured in one phase to those produced by the same assay of liquid media containing known amounts of the ligand under determination.

The improved method generally comprises the steps of (a) contacting the liquid test medium with reagent means which includes a labeled constituent comprising a conjugate of a reactant as defined herein, as labeling substance, and a binding component and which forms, with the ligand to be determined, a binding reaction system producing a bound-phase and a free-phase of said labeled constituent, the quantity of said labeling substance resulting in said bound-phase being a function of the amount of the ligand present in the test medium; (b) separating said bound-phase from said free-phase; and (c) determining the quantity of said reactant in said bound- or free-phase, and thereby the amount of the ligand in the test medium, by assessing the reactant activity therein. As will be more fully discussed hereinafter, the binding reaction system may take the form of any of the known conventional techniques such as those employed in radioimmunoassay systems and in heterogeneous enzyme immunoassay systems.

The monitoring reaction system preferably is enzyme-catalyzed. Usually, a monitoring reaction system is selected which is highly sensitive to the reactant in the conjugate. Luminescent or fluorescent reaction systems are very useful in this regard. Particularly preferred are cyclic reaction systems, especially those in which the reactant is the cycled material. Of the preferred cyclic reaction systems, those which are enzyme-catalyzed are particularly advantageous. The reactant in the conjugate is usually an enzymatic reactant, such as an enzyme substrate or, as is particularly preferred, a coenzyme, and preferably has a molecular weight of less than 9000.

DESCRIPTION OF THE PREFERRED EMBODIMENTS

In the context of this disclosure, the following terms shall be defined as follows: ligand is the substance, or group of substances, whose presence or the amount thereof in a liquid medium is to be determined; specific binding partner of the ligand is any substance, or group of substances, which has a specific binding affinity for the ligand to the exclusion of other substances; and specific binding analog of the ligand is any substance, or group of substances, which behaves essentially the same as the ligand with respect to the binding affinity of the specific binding partner for the ligand.

The specific binding reagent means may take many different forms. In general, such means comprises three basic constituents, which are (1) the ligand to be detected, (2) a specific binding partner of the ligand, and (3) a labeled constituent which is normally a labeled form of (a) the ligand, (b) a specific binding analog of the ligand, or (c) the specific binding partner. The binding reaction constituents are combined simultaneously or in a series of additions, and with an appropriate incubation period or periods the labeled constituent becomes bound to its corresponding competing binding partners such that the extent of binding, i.e. the ratio of the amount of labeled constituent bound to a binding partner to that unbound, is a function of the amount of ligand present. To follow is a brief description of some of the different binding reaction schemes that may be used in carrying out the method of the present invention.

While in conventional heterogeneous specific binding assay methods, such as radioimmunoassays and heterogeneous enzyme immunoassays, the labeling characteristic in the labeled conjugate, such as radioactivity or enzymatic activity, is essentially the same for the bound- and free-forms of the conjugate, according to the present method, the activity of the reactant, as labeling substance, is in certain cases affected by binding of the labeled conjugate. In such a situation the monitoring reaction exhibits a relatively constant character where the ligand is absent from the liquid medium, or is present in an insignificantly small amount. When the ligand is present in the liquid medium, a characteristic or property of the monitoring reaction would be altered. Generally, the activity of the conjugated reactant would be the extent or rate at which the reactant is capable of participating in the monitoring reaction. Thus, the character of the monitoring reaction would be altered by the presence of the ligand in the liquid medium, usually with respect to either the aggregate reaction rate thereof or the equilibrium quantity of one or more reaction products produced thereby. Usually, in this situation, the ability of the conjugated reactant to participate in the monitoring reaction is decreased upon reaction between the specific binding substance to which it is conjugated and a specific binding counterpart of such specific binding substance, that is, the conjugate in its free state is more active in the monitoring reaction than in its bound state For the diagrams which are set out hereinafter, the following legend shall apply:

| Symbol | Definition |
| --- | --- |
| L | ligand to be detected |
| Ⓛ | lingand or specific binding analog thereof |
| B | binding partner for the ligand |
| * | labeling substance, i.e. reactant |
| ⊢ | insoluble phase |
| ⟶ | incubation period followed by appropriate separation |
| (lim) | limited; present in an amount less than that capable of being bound to the total available binding sites under the selected reaction conditions during the selected incubation period; i.e. the constituent for which the other constituents compete for binding |
| (exc) | excess, present in an amount greater than that capable of being bound by the total available binding sites under the selected reaction conditions during the selected incubation period |

HETEROGENEOUS ASSAY SCHEMES

1. Competitive binding formats

L+Ⓛ*+B(lim)→+insolubilizing agent for B or Ⓛ*  (a)

This is the classical competitive binding approach. Examples of such insolubilizing agents are specific precipitating antibodies, specific insolubilized antibodies, and, where B or Ⓛ* is a proteinaceous material, protein precipitators such as ammonium sulfate, or where B or Ⓛ* is a small adsorbable molecule, dextran coated charcoal. Description of parallel systems may be found in *Biochem. J.* 88:137(1963) and U.S. Pat. No. 3,839,153.

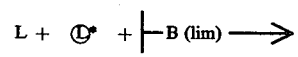  (b)

This approach is commonly referred to as the solid-phase technique. Descriptions of parallel radioimmunoassay and enzyme immunoassay techniques may be found in U.S. Pat. Nos. 3,505,019; 3,555,143; 3,646,346; and 3,654,090.

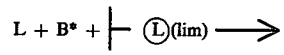  (c)

Reference: U.S. Pat. No. 3,654,090.

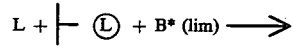  (d)

Reference: U.S. Pat. No. 3,850,752.

2. Sequential saturation formats

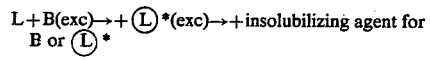  (a)

In the sequential saturation technique, some or all the binding sites on B remaining after the first incubation period are bound by the labeled constituent.

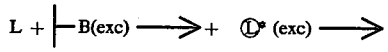  (b)

Descriptions of parallel radioimmunoassay and enzyme immunoassay techniques may be found in U.S. Pat. No. 3,720,760 and *J. Immunol.* 209:129(1972).

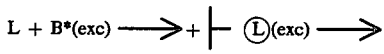  (c)

3. "Sandwich" format

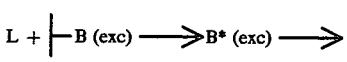

In the sandwich technique, some or all of the ligand molecules bound to the insolubilized binding partners are bound by the labeled constituent.
Reference: U.S. Pat. No. 3,720,760.

4. Solid-phase dilution format

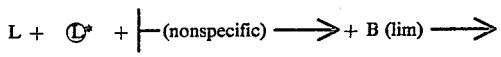

In this technique, the ligand and the labeled constituent are bound to a non-specific binder and thereafter proportional amounts are dissociated therefrom by binding with a binding partner having a greater affinity for the ligand and the labeled constituent. The most useful form of this technique employs a column of the non-specific binder as described in U.S. Pat. No. 3,659,104. Such a technique is useful where the ligand is bound to endogenous binding substances in the sample which unless removed would interfer with the competitive binding reaction. Upon being bound to the non-specific binder, the endogenous binding substances may be removed by appropriate washes.

For further discussion of the parameters involved in conventional heterogeneous assay systems, such as more detailed descriptions of assay formats and alternative separation techniques, reference may be had to *Principles of Competitive Protein-Binding Assays*, ed. Odell and Daughaday (J. B. Lippincott Co., Philadelphia, 1972).

It is contemplated that manipulative schemes involving other orders of addition and other binding reaction formats may be devised for carrying out heterogeneous specific binding assays without departing from the inventive concept embodied herein.

The step of assessing the activity of the conjugated reactant as a constituent of the predetermined monitoring reaction system in either of the bound- or free-phases is conveniently accomplished by contacting such phase with at least one substance which forms with the conjugated reactant, the monitoring reaction, and measuring a characteristic of such reaction. The monitoring reaction system may comprise a single chemical transformation or a plurality or series of chemical transformations.

Where an enzyme-catalyzed reaction system is used, it includes, in addition to the conjugated reactant, at least one enzyme and may include one or more enzymatic reactants such as substrates and coenzymes. Such enzyme-catalyzed reaction system may comprise a single simple enzymatic reaction or a complex series of enzymatic and non-enzymatic reactions. For instance, the enzyme-catalyzed reaction system may consist of a single enzyme-catalyzed degradation or dissociation reaction. In such a system, the conjugated reactant is the enzyme substrate which undergoes degradation or dissociation, and the only component of the reaction system necessary to be contacted with the selected bound- or free-phase is an enzyme which catalyzes the degradation or dissociation reaction. A more complex enzyme-catalyzed reaction system may consist of a single enzymatic reaction involving two or more reactants or may consist of a series of reactions involving several reactants, at least one of which reactions is enzyme-catalyzed. In such a system, the conjugated reactant would be one of the enzymatic reactants in the enzyme-catalyzed reaction and the selected bound- or free-phase would be contacted with the appropriate enzyme and reactant constituents, other than that in the conjugate, necessary to provide the selected enzyme-catalyzed reaction system.

It is further contemplated that the enzyme-catalyzed reaction system may comprise a biochemical system as complex as the metabolic system of a biological cell such as a microorganism. For example, a nutrient substance essential to the growth of a particular microorganism may be selected as the reactant in the conjugate. Reactant activity would be measurable by monitoring a characteristic of the microorganism, such as the rate of microorganism growth, when such microorganism would be placed in an environment wherein the only source of the reactant nutrient substance is the conjugate.

The appropriate reaction constituents which form, together with the reactant in the conjugate, the monitoring reaction system may be contacted with the selected separated phase mixture singularly or in any combination either prior to, simultaneous with, or subsequent to initiation of the specific binding reaction. After initiation of the specific binding reaction, the reaction mixture, which may include any or all of the necessary components for the monitoring reaction is usually incubated for a predetermined period or periods of time before separation of the resulting bound- and free-phases. After separation, any components which are necessary for the monitoring reaction and which are not already present in sufficient quantities in the selected separated phase are added thereto, and reactant activity therein is assessed as an indication of the presence or amount of the ligand in the liquid medium.

When the reaction rate of the monitoring reaction is the characteristic used to assess reactant activity in the selected bound- or free-phase, as is preferred, such rate is usually determined by measuring the rate of disappearance of a reactant or the rate of appearance of a reaction product. Such measurement can be accomplished by a wide variety of methods including the conventional chromatographic, gravimetric, potentiometric, spectrophotometric, fluorometric, turbidimetric, and volumetric analysis techniques. Since the present method is primarily designed for the detection of low concentrations of ligands, highly sensitive reaction systems have been developed for use in conjunction with the novel specific binding reaction system.

One preferred form of the monitoring reaction includes a luminescent reaction system, preferably enzyme-catalyzed, such as a reaction exhibiting the phenomenon of bioluminescence or chemiluminescence. The reactant in the conjugate may be a reactant in either the light-producing reaction or a reaction which is preliminary to an enzymatic or non-enzymatic luminescent reaction. The activity of the conjugated reactant can be assessed by following the rate of light production or the total amount, peak intensity, or character of the light produced. Examples of luminescent reaction systems are given in Table A in which the following abbreviations are used:

ATP: adenosine triphosphate
AMP: adenosine monophosphate
NAD: nicotinamide adenine dinucleotide
NADH: reduced nicotinamide adenine dinucleotide
FMN: flavin mononucleotide
$FMNH_2$: reduced flavin mononucleotide
hν: electromagnetic radiation, usually in the infrared, visible, or ultraviolet region

TABLE A

| Luminescent Reaction System | Conjugated Reactant |
|---|---|
| A. ATP + reduced luciferin $\xrightarrow{\text{luciferase (fire fly)}}$ h$\nu$ + AMP + oxidized luciferin | ATP or reduced luciferin |
| B. FMNH$_2$ + long-chain aldehyde + O$_2$ $\xrightarrow{\text{luciferase (P. fisheri)}}$ h$\nu$ FMN + long-chain acid + H$_2$O | FMNH$_2$ or long-chain aldehyde |
| C. (1) NADH + FMN + H$^\oplus$ $\xrightarrow{\text{NADH dehydrogenase}}$ NAD + FMNH$_2$<br><br>(2) FMNH$_2$ + long-chain aldehyde + O$_2$ $\xrightarrow{\text{luciferase (P. fisheri)}}$ h$\nu$ + FMN + long-chain acid + H$_2$O | NADH or FMN |
| D. (1) 3',5'-adenosine diphosphate + reduced luciferin sulfate $\xrightarrow{\text{sulfate transferase}}$ adenosine-3'-phosphate-5'-phosphosulfate + reduced luciferin<br><br>(2) reduced luciferin + O$_2$ $\longrightarrow$ h$\nu$ + oxidized luciferin | 3'5'-adenosine diphosphate or reduced luciferin |
| E. luminol + H$_2$O$_2$ $\xrightarrow{\text{peroxidase*}}$ h$\nu$ + aminophthalate + N$_2$ | luminol |
| F. reduced pyrogallol + H$_2$O$_2$ $\xrightarrow{\text{peroxidase*}}$ h$\nu$ + oxidized pyrogallol + H$_2$O | reduced pyrogallol |
| G. luminol + O$_2$ $\xrightarrow{\text{oxygenase}}$ h$\nu$ + aminophthalate + N$_2$ | luminol |
| H. reduced pyrogallol + O$_2$ $\xrightarrow{\text{oxygenase}}$ h$\nu$ + oxidized pyrogallol | reduced pyrogallol |
| I. isoluminol + H$_2$O$_2$ $\xrightarrow{\text{lactoperoxidase}}$ h$\nu$ + aminophthalate + N$_2$ | isoluminol |
| J. isoluminol + KO$_2$ $\longrightarrow$ h$\nu$ + aminophthalate + N$_2$ | isoluminol |

*or catalase

Further details and discussion concerning luminescent reaction systems which may be used in the present method may be found in the following references:

J. Biol. Chem. 236:48(1961).
J. Amer. Chem. Soc. 89:3944(1967).
Cornier et al. Bioluminescence in Progress, ed. Johnson et al., Princeton University Press (New Jersey, 1966) pp. 363-84.
Kries, P. Purification and Properties of Renilla Luciferase, doctoral thesis University of Georgia (1967).
Am. J. Physiol. 41:454(1916).
Biol. Bull. 51:89(1926).
J. Biol. Chem. 243:4714(1968).

Another type of preferred, sensitive, monitoring reaction involves the phenomenon of fluorescence and is enzyme catalyzed. In such a reaction system the reactant in the conjugate is a substrate in an enzymatic reaction which produces a product which has a fluorescent property which distinguishes it from the conjugated substrate. A general reaction scheme for such an enzyme catalyzed reaction system is as follows:

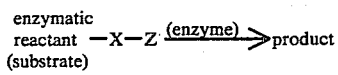

$$\text{enzymatic reactant (substrate)} -X-Z \xrightarrow{\text{(enzyme)}} \text{product}$$

wherein X is an enzyme-cleavable bond or linking group, such as an ester or amido group, and Z is a specific binding substance which, depending upon the specific binding reaction technique used, is the ligand, a specific binding analog of the ligand, or a specific binding partner of the ligand. Specific conjugates which may be used in this type of reaction system are various enzyme-cleavable modifications and derivatives of fluorescein, umbelliferone, 3-indole, $\beta$-naphthol, 3-pyridol, resorufin, and so forth. Examples of possible structural formulas of such derivatives are as follows:

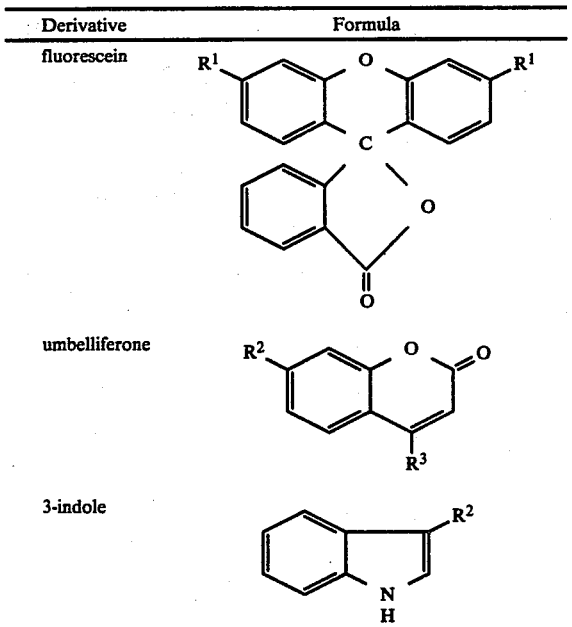

| Derivative | Formula |
|---|---|
| fluorescein | |
| umbelliferone | |
| 3-indole | |

-continued

| Derivative | Formula |
|---|---|
| β-naphthol | ![naphthol structure with R²] |
| 3-pyridol | ![pyridol structure with R²] |
| resorufin | ![resorufin structure with R²] | wherein R¹ is —OH or —X—Z (as defined above in this paragraph), R² is —X—Z, and R³ is —H or —CH₃.

A reaction system which is particularly preferably for use in assessing the activity of the conjugated reactant in the selected separated phase is a cyclic or cycling reaction system. Such a reaction system is one in which a product of a first reaction is a reactant in a second reaction, which second reaction has as one of its products a substance that is also a reactant in the first reaction.

The following diagram illustrates a model of a cyclic reaction system:

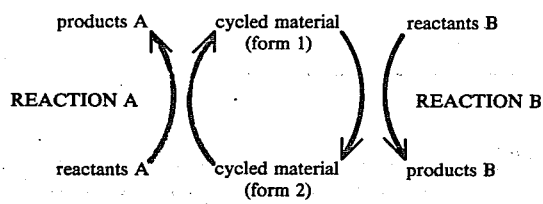

In the above model cyclic reaction system, a small amount of cycled material, if provided with sufficient amounts of reactants A and B, will generate large amounts of products A and B. Since the rate and amount of product produced by the reactions constituting the cyclic reaction system is highly sensitive to the amount of cycled material present, it is most preferred to use the cycled material as the reactant in the conjugate of the present invention. Examples of cycling reaction systems contemplated for use in conjunction with the novel specific binding reaction system of the present invention are given in Tables B, C, and D.

TABLE B product A ⇌ NAD* ⇌ reactant B
       enzyme   enzyme
reactant A ⇌ NADH** ⇌ product B

| reaction | reactant A or product B | enzyme | reactant B or product A |
|---|---|---|---|
| 1 | lactaldehyde | alcohol dehydrogenase | propanediol |
| 2 | α-ketoglutarate + NH₃ | glutamic dehydrogenase | glutamate |
| 3 | oxaloacetate | malic dehydrogenase | malate |
| 4 | acetaldehyde | alcohol dehydrogenase | ethanol |
| 5 | α-ketoglutarate + CO₂ | isocitric dehydrogenase | isocitrate |
| 6 | dihydroxyacetone phosphate | α-glycerol phosphate dehydrogenase | L-α-glycerol phosphate |
| 7 | pyruvate | lactic dehydrogenase | lactate |
| 8 | 1,3-diphosphoglycerate | glyceraldehyde-3-phosphate dehydrogenase | glyceraldehyde-3-phosphate + phosphate |

*nicotinamide adenine dinucleotide
**reduced NAD

TABLE C product A ⇌ NADP* ⇌ reactant B
       enzyme   enzyme
reactant A ⇌ NADPH** ⇌ product B

| reaction | reactant A or product B | enzyme | reactant B or product A |
|---|---|---|---|
| 1 | 6-phosphogluconate | glucose-6-phosphate dehydrogenase | glucose-6-phosphate |
| 2 | oxidized glutathione | glutathione reductase | reduced glutathione |
| 3 | p-benzoquinone | quinone reductase | hydroquinone |
| 4 | nitrate | nitrate reductase | nitrite |
| 5 | α-ketoglutarate + NH₃ | glutamic dehydrogenase | glutamate |

*nicotinamide adenine dinucleotide phosphate
**reduced NADP

It should be noted that the cyclic reaction systems illustrated in Tables B and C comprise the combination of any one of the reactions listed in the respective tables with any other reaction listed therein. For example, reaction 1 in Table B may be paired with any one of reactions 2-8 to form a useful cyclic reaction system. Thus, Tables B and C represent respectively 56 and 20 possible cyclic reaction systems for use in the present invention.

In addition to the cyclic reaction systems represented in Tables B and C, it is contemplated that one of the reactions in the cyclic reaction system may involve the enzymatic or non-enzymatic conversion of a spectrophotometric indicator, preferably colorimetric. An example of a cyclic reaction system involving a conversion of an indicator is the system produced by combining one of the reactant B-product B reactions from Table B with a reaction comprising an oxidation-reduction indicator and an electron transfer agent. As electron transfer agent, phenazinemethosulfate may be used. Useful indicators include the oxidized forms of nitrotetrazolium, thiazolyl blue, and dichlorophenolindophenol.

TABLE D

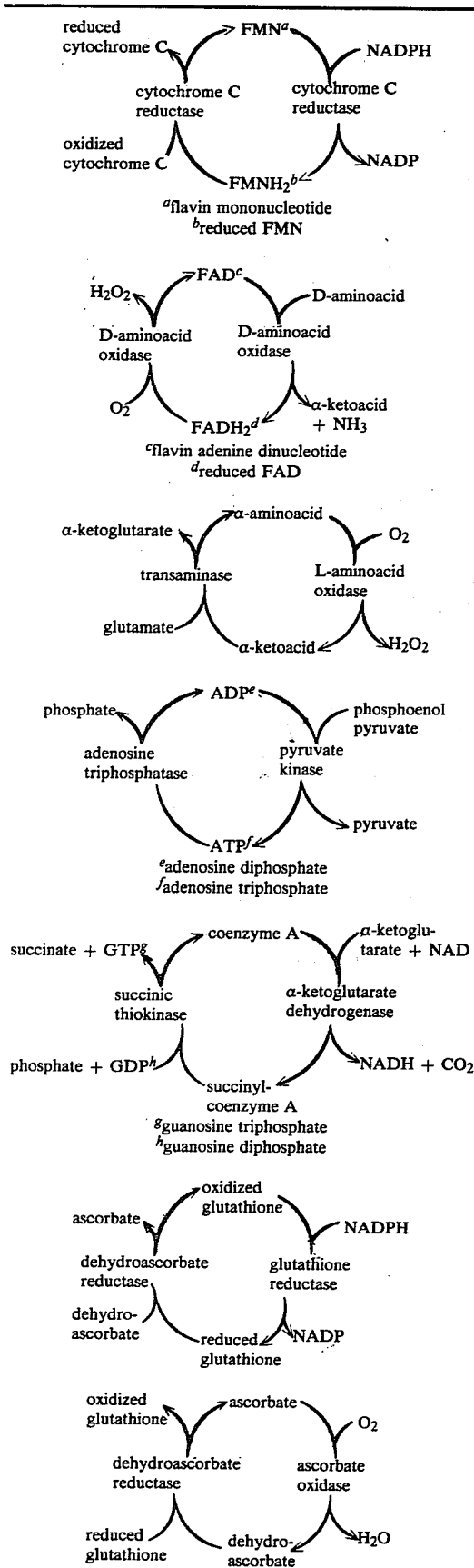

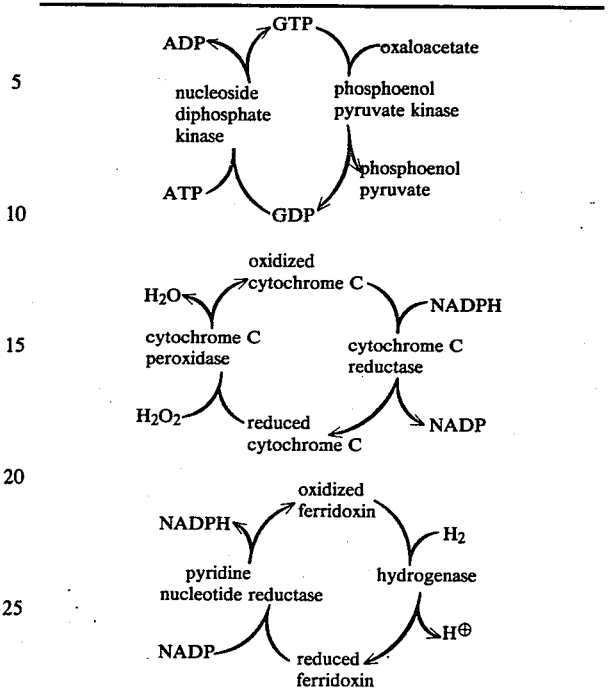

TABLE D-continued

In forming any of the cyclic reaction systems illustrated in Tables B, C, and D, where a component in the reaction system is in an ionic form, it may of course be added in a salt or acid form which is ionizable upon contacting the liquid medium. A water soluble salt or acid of such component is usually preferred.

It is also contemplated that an exponential cyclic reaction system may be included in the monitoring reaction system. An example of an exponential cyclic reaction system is as follows:

$$AMP + ATP \xrightarrow{myokinase} 2\ ADP$$

$$ADP + PEP \xrightarrow{pyruvate\ kinase} ATP + pyruvate$$

Such a cyclic reaction is autocatalytic in the sense that during each cycle the amount of cycled material is doubled. The cycling rate therefore increases exponentially with time and affords a high degree of sensitivity. Further details and discussion relating to such cyclic reactions may be found in *J. Biol. Chem.* 247:3558-70(1972).

Where a cyclic reaction system is used as a means of assessing any change in activity of the conjugated reactant, the rate of disappearance of a reactant or rate of appearance of a reaction product can be determined by conventional techniques or by using one or more additional cycling systems followed by a conventional determination of the aggregate reaction rate.

The use of a cyclic reaction system is conjunction with the heterogeneous specific binding reaction system provides a high degree of assay versatility as well as sensitivity. A single reactant-specific binding substance conjugate may be used with a ultiplicity of reactions to form cyclic systems which have sensitivities varying over a wide range and which provide a wide variety of responses detectable by the senses or artificial means. Such versatility is lacking in the prior art.

The present invention may be applied to the detection of any ligand for which there is a specific binding partner. The ligand usually is a peptide, protein, carbohydrate, glycoprotein, steroid, or other organic molecule for which a specific binding partner exists in biological systems or can be synthesized. The ligand, in functional terms, is usually selected from the group consisting of antigens and antibodies thereto; haptens and antibodies thereto; and hormones, vitamins, metabolites and pharmacological agents, and their receptors and binding substances. Specific examples of ligands which may be detected using the present invention are hormones such as insulin, chorionic gonadotropin, thyroxine, liothyronine, and estriol; antigens and haptens such as ferritin, bradykinnin, prostaglandins, and tumor specific antigens; vitamins such as biotin, vitamin $B_{12}$, folic acid, vitamin E, and ascorbic acid; metabolites such as 3',5' adenosine monophosphate and 3',5' guanosine monophosphate; pharmacological agents such as dilantin, digoxin, morphine, digitoxin, and barbiturates; antibodies such as microsomal antibody and antibodies to hepatitis and allergens; and specific binding receptors such as thyroxine binding globulin, avidin, intrinsic factor, and transcobalamine.

In the conjugate of the present invention, the reactant is coupled or bound to a specific binding substance, which is the ligand, a specific binding analog of the ligand, or a specific binding partner of the ligand, depending upon the assay scheme selected, such that a measurable amount of activity of the reactant is retained. The bond between the reactant and the specific binding substance is usually substantially irreversible under the conditions of the assay such as where the predetermined monitoring reaction in which the reactant has activity is not designed to chemically destroy such bond as in the above-mentioned luminescent and cyclic reaction systems. However, in certain instances such bond is by design destroyed or otherwise affected by the selected monitoring reaction as a means for assessing in reactant activity. Such a case is the enzymatic fluorescent substrate reaction systems referred to previously herein.

The reactant may be directly coupled to the specific binding substance so that the molecular weight of the conjugate is less than or equal to the aggregate molecular weight of the reactant and the specific binding substance. Usually, however, the reactant and the specific binding substance are linked by a bridge group comprising between 1 and 50, and preferably between 1 and 10, carbon atoms or heteroatoms such as nitrogen, oxygen, sulfur, phosphorus and so forth. Examples of a bridge group comprising a single atom would be a methylene group (one carbon atom) and an amino group (one heteroatom). The bridge group usually has a molecular weight not exceeding 1000 and preferably less than 200. The bridge group comprises a chain of carbon atoms or heteroatoms, or a combination of both, and is joined to the reactant and the specific binding substance, or active derivative thereof, by a connecting group usually in the form of an ester, amido, ether, thioester, thioether, acetal, methylene, or amino group.

The reactant in the conjugate of the present invention may be any substance which has given (i.e. fixed or known) reactant activity as a constituent of a predetermined monitoring reaction. More particularly, for the purposes of this disclosure, the terms "reactant" and "substance having reactant activity" refer to any chemical substance which is capable of undergoing a finite measurable chemical transformation which yields one or more products different from itself and which results upon interaction of said reactant with reaction-initiating means, such as a chemical substance (i.e. another reactant, a catalyst, or other type tion), electromagnetic radiation, thermal energy, or sonic energy. The class of substances defined herein as "reactants" therefore includes conventional inorganic and organic reagents and various biochemical materials, but excludes such materials as catalysts, including enzymes, and radioactive isotopes which are not reactants in the monitoring reaction. It will be recognized that while a particular chemical substance may be classified in several different catagories because it is able to function in several ways depending on its chemical environment, it is the activity of such substance with respect to the selected monitoring reaction referred to herein which shall govern which functional identity such substance shall have in the context of this disclosure.

Preferably, the reactant is an enzymatic reactant such as an enzyme substrate, a coenzyme, or an active modification or derivative thereof. An enzyme substrate is a compound or moiety capable of undergoing a chemical transformation that is catalyzed by an enzyme. Where a substrate is employed as the conjugated reactant, the preferred molecular weight thereof is less than 9000 and preferably less than 5000. Substrates of such size, because of their lack of molecular complexity, are most convenient for use in the fabrication of the conjugate. Examples of enzyme substrates which are contemplated for use in the present invention include the enzyme-cleavable fluorescent substrates referred to previously such as fluroescein and umbelliferone derivatives; pH indicators; and spectrophotometric indicator dyes, particularly chromogenic types.

For the above reasons and for reasons of versatility and adaptability, coenzymes are especially preferred for use as the reactant in the conjugate. A coenzyme is a nonprotein molecule which migrates from one enzyme protein to another in facilitating the efficient performance of the catalytic function of the enzyme. All known coenzymes have a molecular weight of less than 9000, the preferred coenzymes having a molecular weight of less than about 5000. Useful coenzymes include the nucleotide coenzymes, particularly those comprising adenine groups, such as the adenosine phosphates (i.e. the mono-, di-, and tri-phosphate forms), nicotinamide adenine dinucleotide and its reduced forms, and nicotinamide adenine dinucleotide phosphate and its reduced forms. Other useful coenzymes include the guanosine phosphates, flavin mononucleotide and its reduced forms, flavin adenine dinucleotide and its reduced forms, coenzyme A and its thioesters including succinyl-coenzyme A, 3',5' adenosine diphosphate, and adenosine-3'-phosphate-5'-phosphosulfate.

Useful coenzyme-active conjugates comprise nucleotide coenzymes having an adenine group to which the specific binding substance, i.e., a ligand, a specific binding analog of a ligand, or a specific binding partner of a ligand, is coupled through a direct bond or a bridge group as referred to hereinbefore. Such coenzyme-active conjugates which comprise an adenosine phosphate, nicotinamide adenine dinucleotide or its reduced form, or nicotinamide adenine dinucleotide phosphate or its reduced form, have the following general formula:

wherein R¹ is

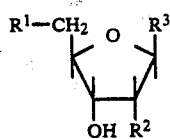

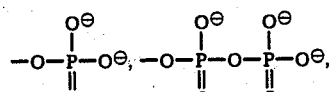

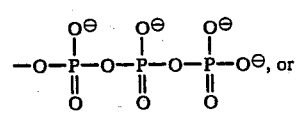

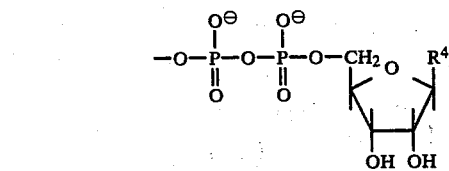

wherein R² is —OH or 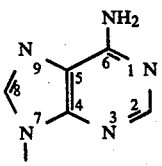;

wherein R³ is

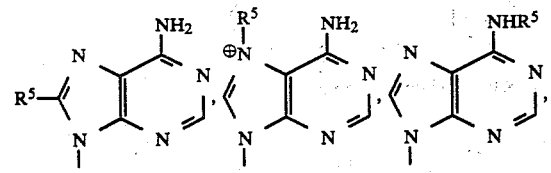

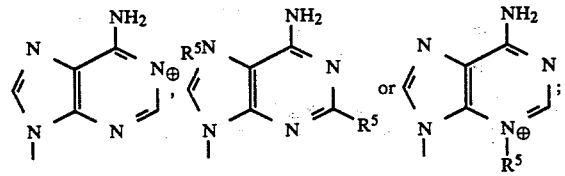

wherein R⁴ is

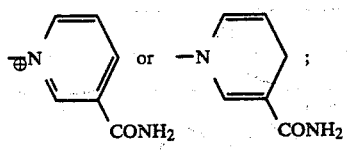

wherein R⁵ is —Y-Z; wherein Y is a bond or a bridge group; and wherein Z is a ligand, a specific binding analog of a ligand, or a specific binding partner of a ligand. The above formula represents the ionized forms of the coenzyme-active conjugate, however, the protonized or acid forms are equally useful. The extent of protonization depends on the pH of the environment. Also, the salts of such conjugates may also be used where appropriate.

Synthesis of such compounds may be accomplished in a variety of ways. It is contemplated that the synthesis routes which are schematically illustrated below are advantageously followed in the preparation of the useful compounds. In the illustrated syntheses, the positions on the adenine ring structure are referred to according to the following:

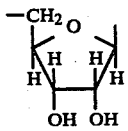

Also, the following abbreviations are used;
Rib refers to the ribose moiety, i.e.,

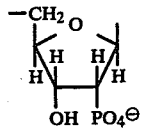

Rib' refers to the phosphated ribose moiety, i.e.,

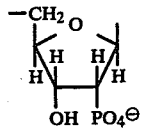

Ph refers to a phosphate group;
AP derivatives refers to derivatives of adenosine-5'-phosphate, i.e., the mono- (AMP), di- (ADP), or tri- (ATP) phosphate form;
NAD derivative refers to a derivative of either nicotinamide adenine dinucleotide or a reduced form thereof;
NADP derivative refers to a derivative of either nicotinamide adenine dinucleotide phosphate or a reduced form thereof;
R refers to the specific binding substance or a modification thereof; and
X refers to a leaving group, usually a halogen.

1-position derivatives of AP

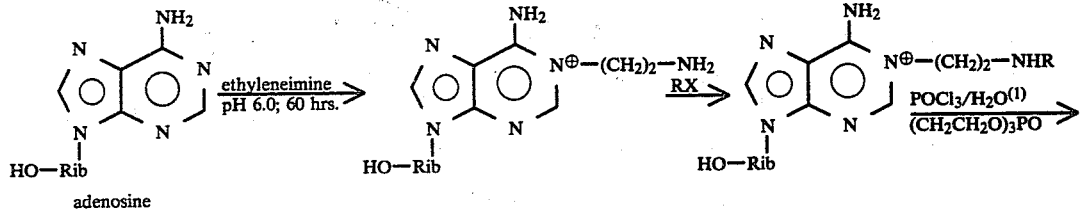

-continued
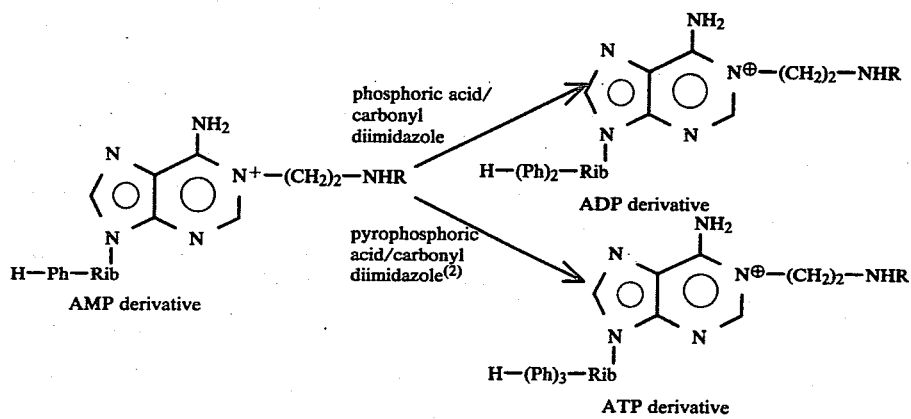
(1)Guilford, H., et al., Chemica Scripta 2:165 (1972).
(2)Trayer, I. P., et al., Biochem. J. 139:609 (1974).
1-position derivative of NAD
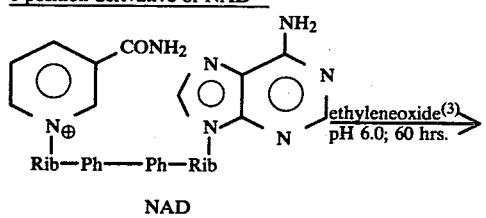
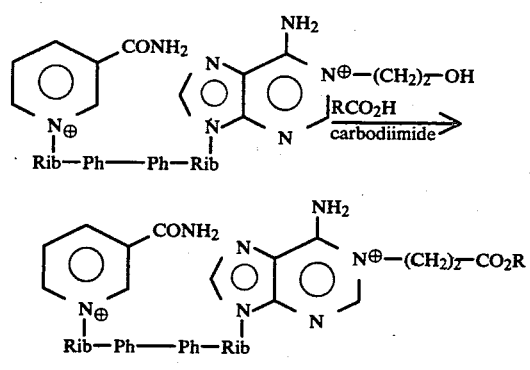
NAD derivative
(3)Windmueller, H.G., and Kaplan, N.O., J. Biol Chem. 236:2716 (1961).
1-position derivative of NADP
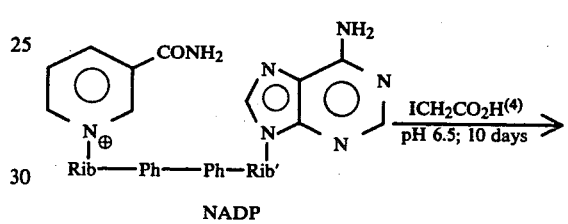
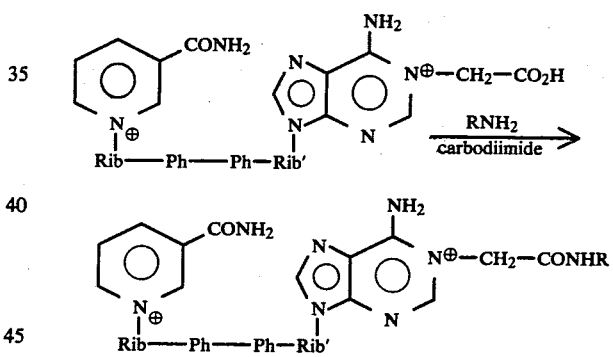
NADP derivative
(4)Lowe, C.R. and Mosbach, K., Eur. J. Biochem. 49:511 (1974).
2-position derivatives of AP
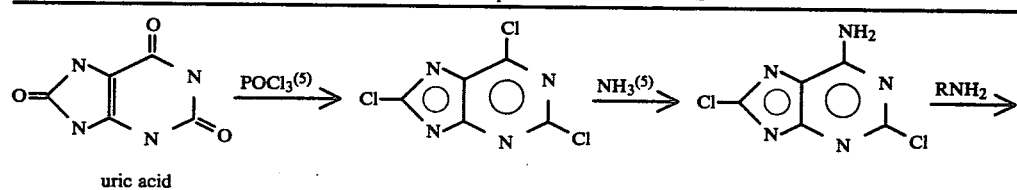
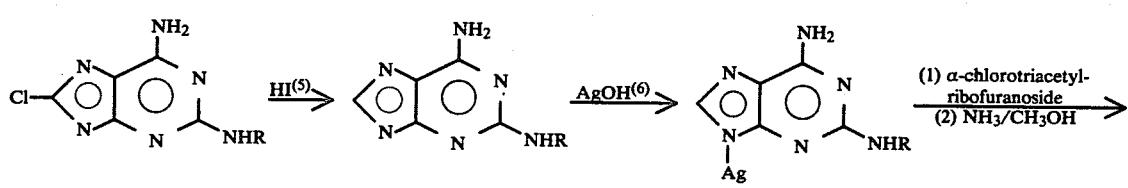

-continued

2-position derivatives of AP

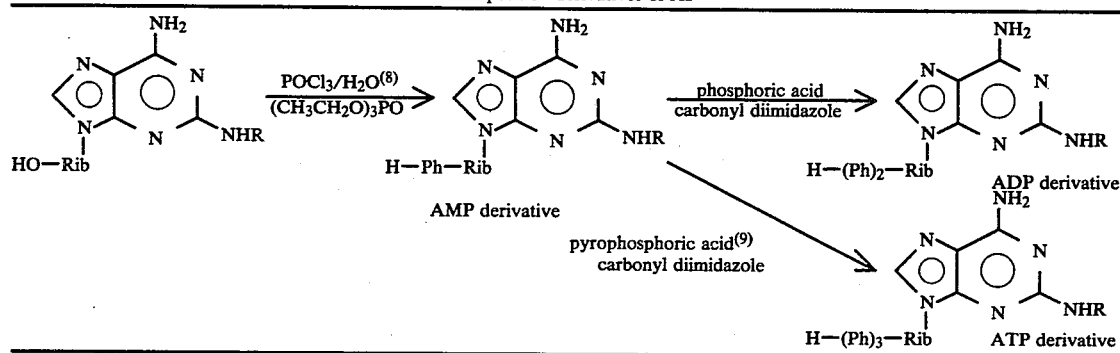

AMP derivative → ADP derivative / ATP derivative

[5] Acheson, R. M., An Introduction to the Chemistry of Heterocyclic Compounds, Interscience Publ. (New York 1962), p. 308.
[6] Fischer, E., Ber. 30:2239 (1897).
[7] Davoll et al., J. Chem. Soc., 967 (1948).
[8] Guilford, H., et al., supra.
[9] Trayer, I. P., et al., supra.

2-position derivative of NAD

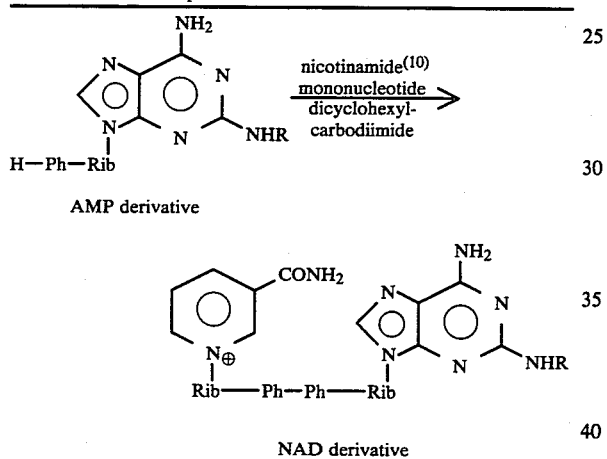

AMP derivative

NAD derivative

[10] Hughes, N. A., et al., J. Chem. Soc., 3733 (1957).

2-position derivative of NADP

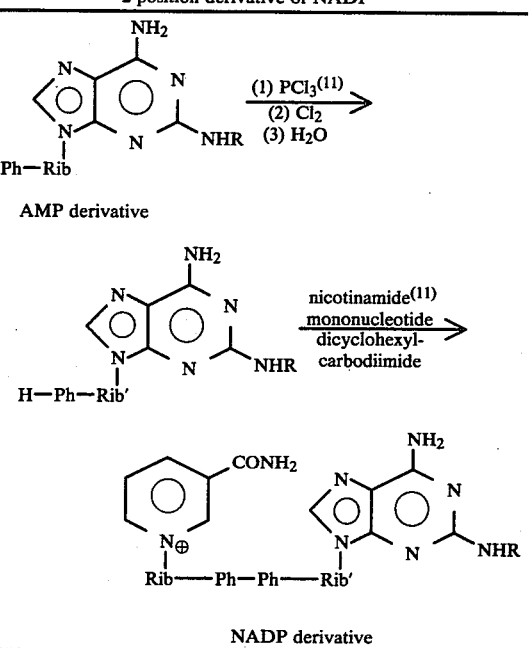

AMP derivative

NADP derivative

[11] Hughes, N. A., et al., supra.

3-position derivatives of AP

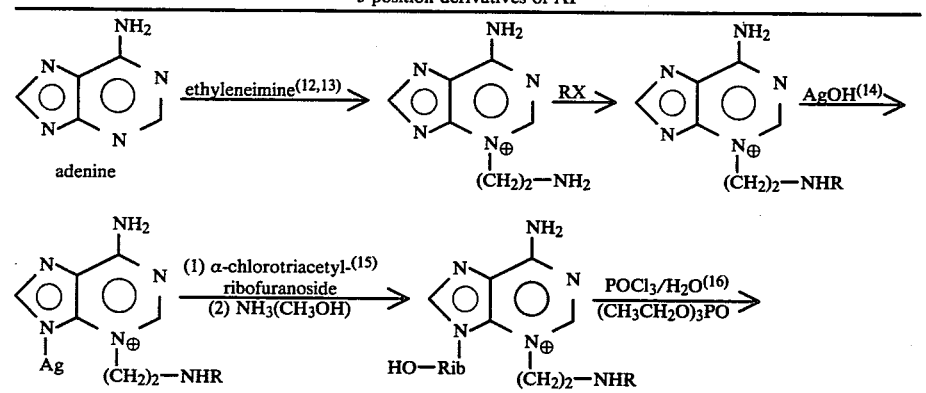

adenine

-continued

3-position derivatives of AP

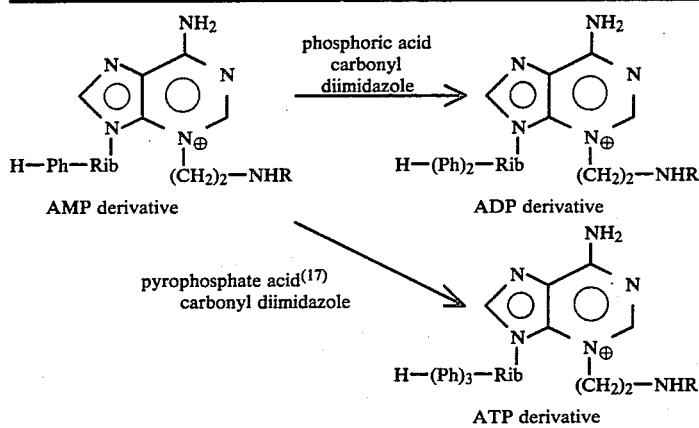

(12) Lister, J. H., in Advances in Heterocyclic Chemistry, ed. Kabritzky et al., Academic Press (New York, 1966), p. 33.
(13) Leonard, N. J., and Fujii, T. J., J. Amer. Chem. Soc. 85:3719 (1963).
(14) Fischer, E., supra.
(15) Davoll et al., supra.
(16) Guilford, H., et al., supra.
(17) Trayer, I. P., et al., supra.

3-position derivative of NADP

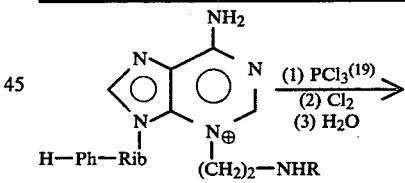

AMP derivative

3-position derivative of NAD

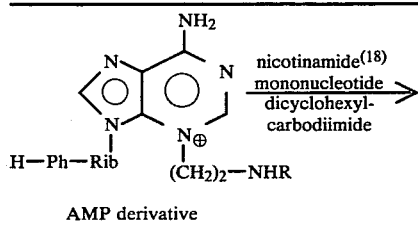

AMP derivative

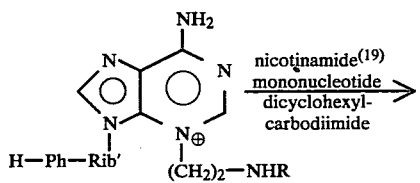

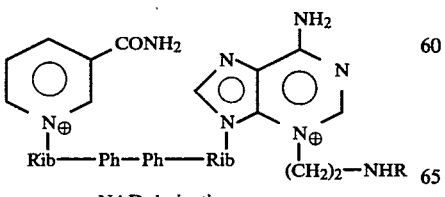

NAD derivative

(18) Hughes, N. A., et al., supra.

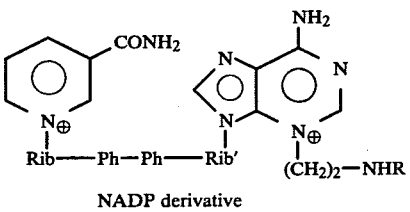

NADP derivative

(19) Hughes, N. A., et al., supra

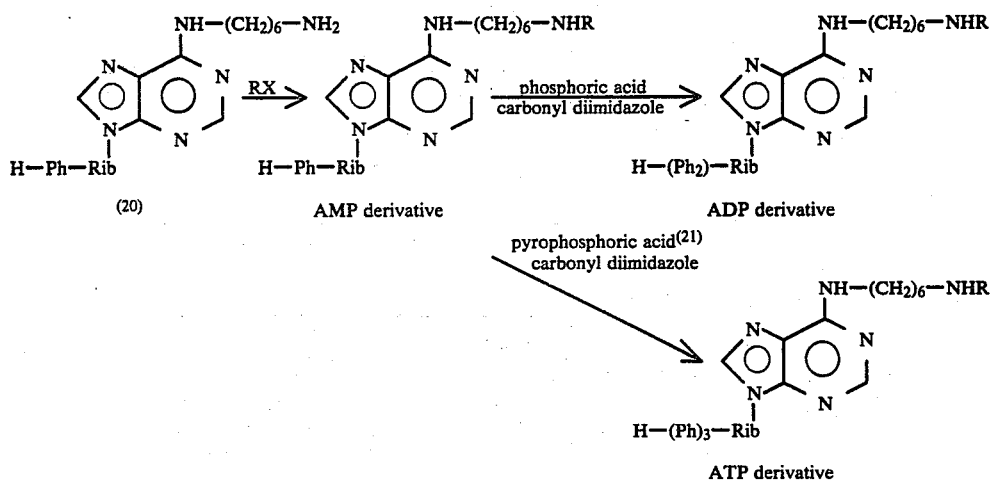
(20) Guilford, H., et al., supra.
(21) Trayer, I. P., et al., supra.
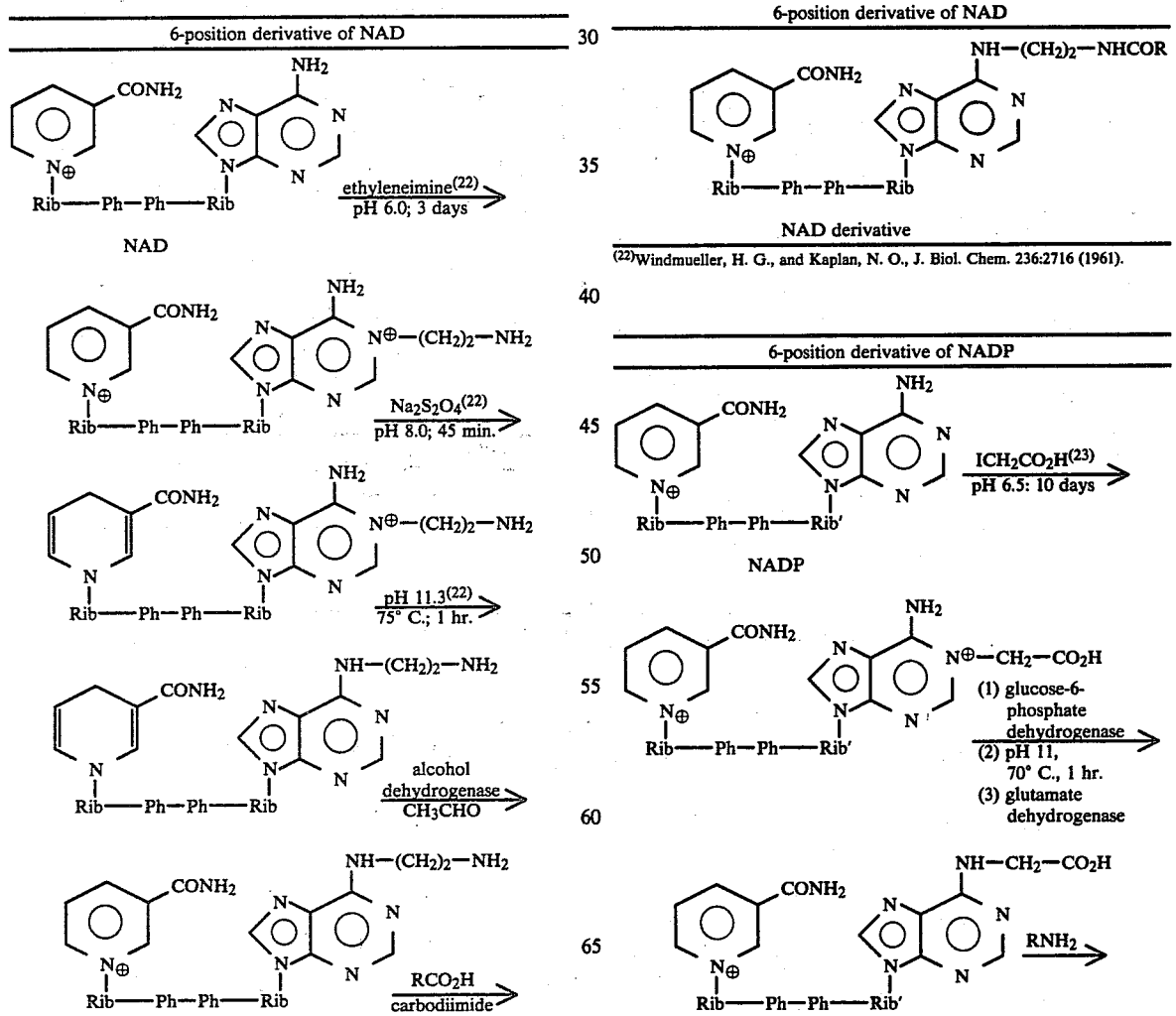
(22) Windmueller, H. G., and Kaplan, N. O., J. Biol. Chem. 236:2716 (1961).

6-position derivative of NADP

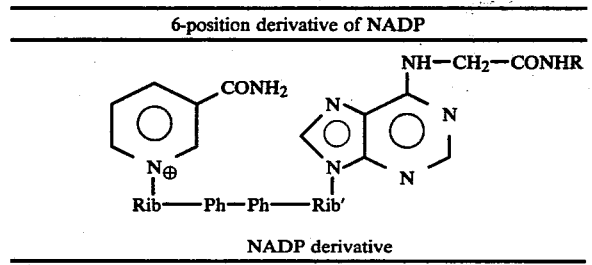

NADP derivative

[23] Lowe, C. R., and Mosbach, K., supra.

8-position derivatives of AP

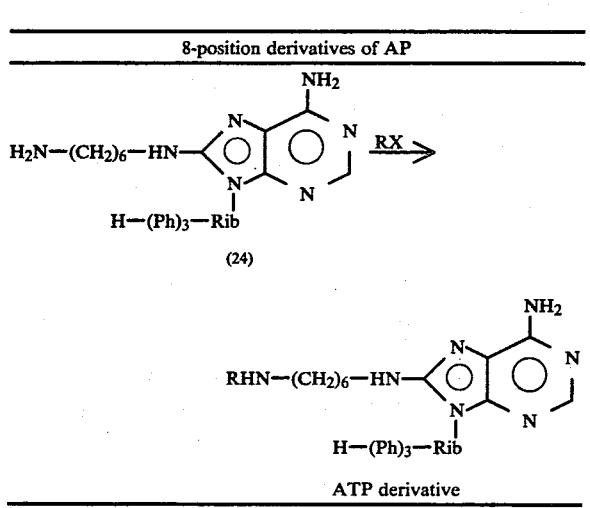

ATP derivative

[24] Trayer, I. P., et al., supra.

8-position derivative of NAD

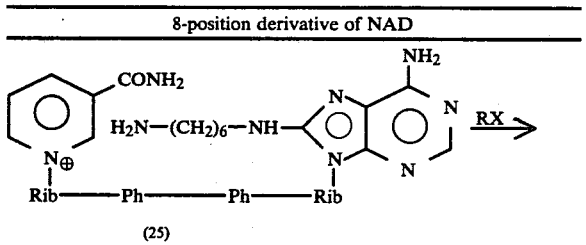

(25)

8-position derivative of NAD

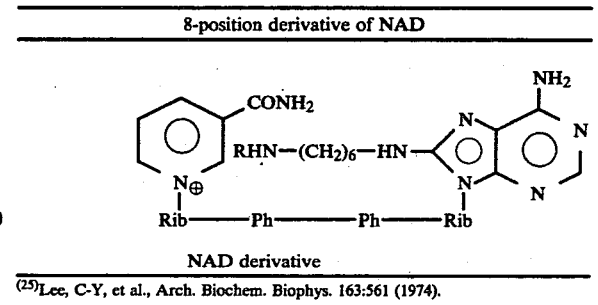

NAD derivative

[25] Lee, C-Y, et al., Arch. Biochem. Biophys. 163:561 (1974).

8-position derivative of NADP

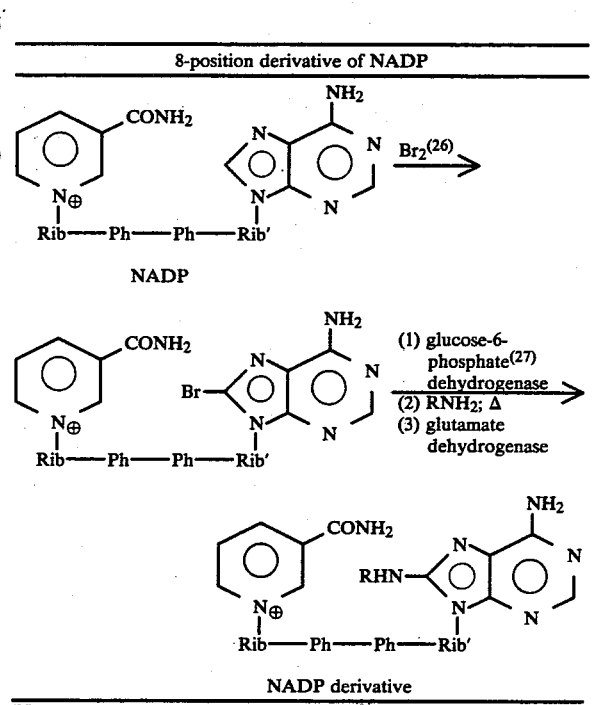

NADP derivative

[26] Lee, C-Y, et al., supra.
[27] Lowe, C. R. and Mosbach, R., supra.

9-position derivatives of AP

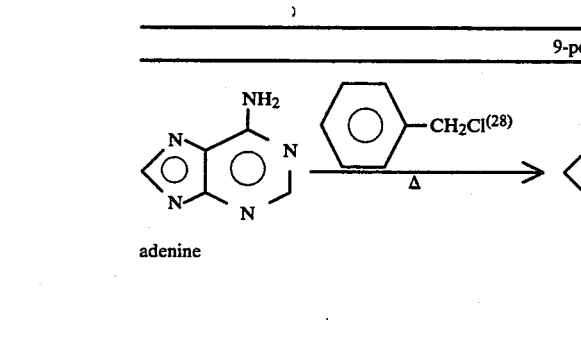
adenine

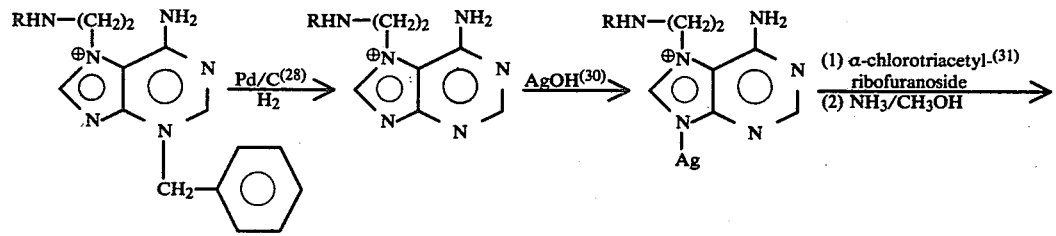

9-position derivatives of AP

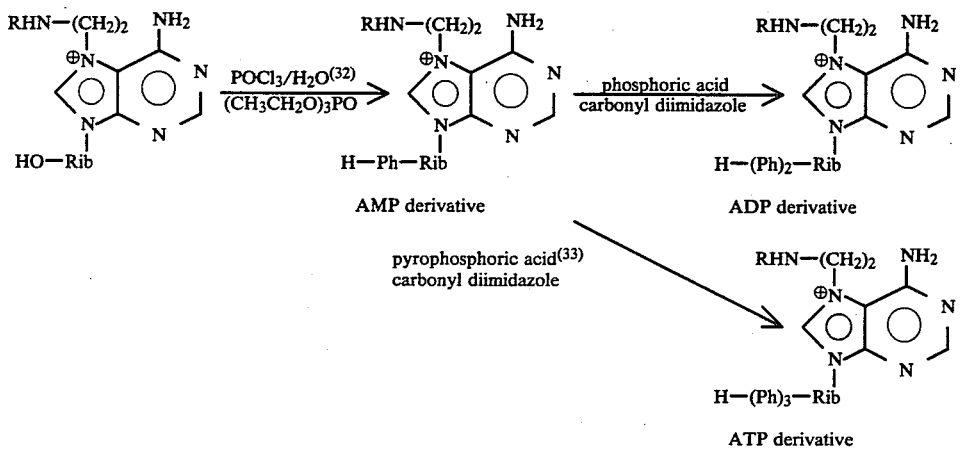

(28)Leonard, N. J., and Fujii, T. J., supra.
(29)Lister, J. H., supra.
(30)Fischer, E., supra.
(31)Davoll, et al., supra.
(32)Guildford, H., et al., supra.
(33)Trayer, I. P., et al., supra.

9-position derivative of NAD

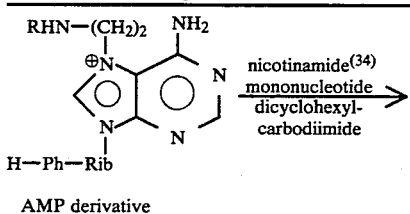

AMP derivative

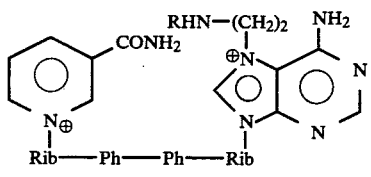

NAD derivative (34)Hughes, N. A., et al., supra.

9-position derivative of NADP

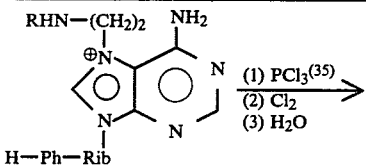

AMP derivative

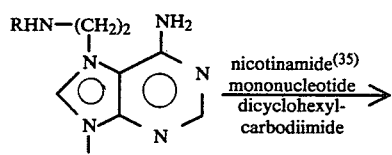

9-position derivative of NADP

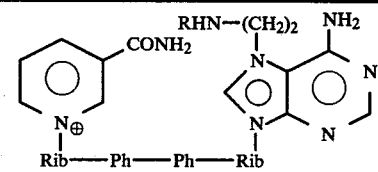

NADP derivative (35)Hughes, N. A., et al., supra.

In addition to the compounds mentioned above, useful coenzyme-active conjugates include the adenosine phosphates to which are coupled the specific binding substance through the phosphate grouping. Such compounds have the following general formula:

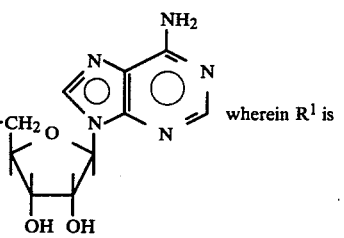

wherein $R^1$ is

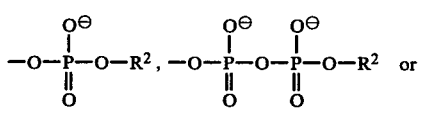

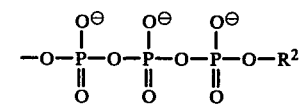

wherein $R^2$ is —Y-Z; wherein Y is a bond or a bridge group; and wherein Z is a ligand, a specific binding analog of a ligand, or a specific binding partner of a ligand. Also, the protonized or acid forms, as well as the salt forms where appropriate, may be used.

Synthesis of such compounds may be accomplished in a variety of ways. It is contemplated that the synthesis routes which are schematically illustrated below are advantageously followed in the preparation of the useful compounds. The abbreviations used hereinbefore also apply to the illustration to follow.

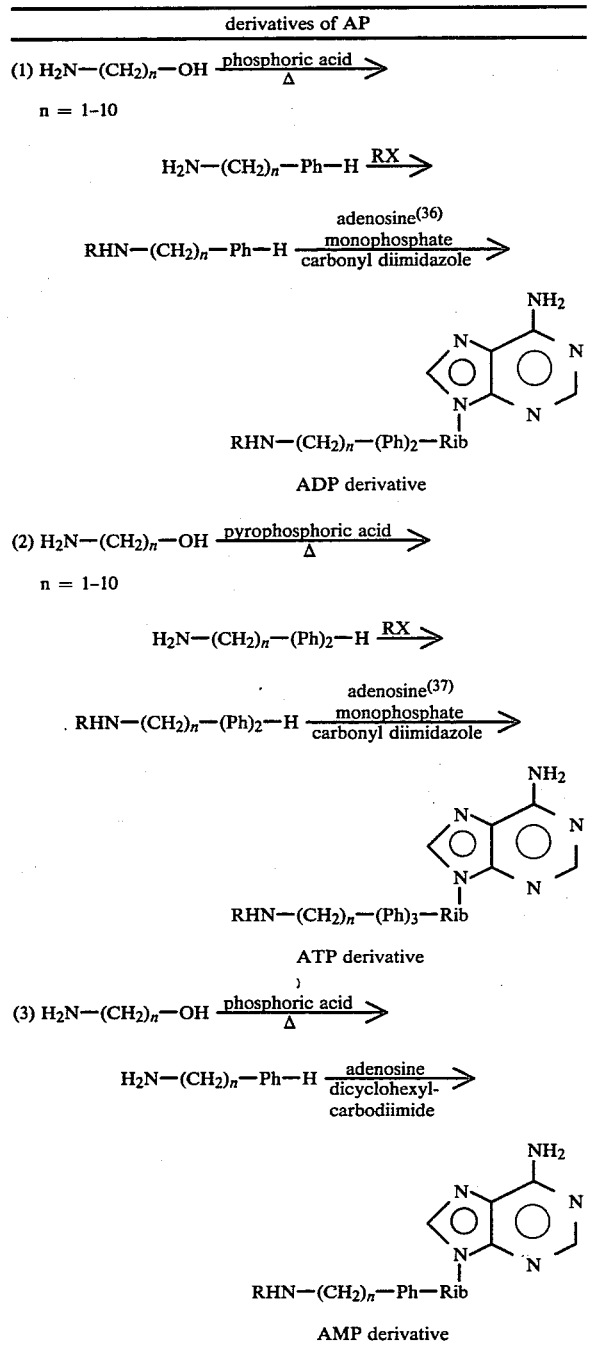

[36]Trayer, I. P., et al., Biochem. J. 139:609 (1974).
[37]Trayer, I. P., et al., supra.

In one form of the present invention, the components of the specific binding reaction which are to be combined with the liquid medium suspected of containing the ligand are in a liquid or solid form. The assay method may be carried out in a standard laboratory vessel such as a test tube with the specific binding reaction components and the components of the reaction system being added thereto in solid or liquid form.

It is also contemplated that one or more of the specific binding reaction components and/or one or more of the components of the monitoring reaction may be incorporated with a carrier. In one aspect, the carrier may be a liquid holding vessel such as a test tube or capsule containing such component or components in an interior portion thereof, for instance, in the form of a liquid or loose solid or a coating on an interior surface of the vessel. In another aspect, the carrier may be in the form of matrix which is insoluble and porous, and preferably absorbent, relative to the liquid medium to be tested. Such matrix may be in the form of bibulous papers; polymeric films, membranes, fleeces, or blocks; gels; and so forth. In such a form, the device would provide a convenient means for contacting the liquid medium to be tested, for carrying out the specific binding reaction and/or the monitoring reaction, for effecting the necessary separation, and for observing the resulting response.

The liquid medium to be tested may be a naturally occurring or artificially formed liquid suspected of containing or known to contain the ligand, and usually is a biological fluid or a liquid resulting from a dilution or other treatment thereof. Biological fluids which may be assayed following the present method include serum, plasma, urine, and amniotic, cerebral, and spinal fluids. Other materials such as solid matter, for example tissue, or gases may be assayed by reducing them to a liquid form such as by dissolution of the solid or gas in a liquid or by liquid extraction of the solid.

In contrast to the prior art assay systems, biological fluids containing substances which have reactant activity similar or identical to that of the conjugated labeling substance may be assayed for the ligand without background interference. Endogenous background reactant activity can be readily eliminated in several manners. The biological fluid can be treated to selectively destroy the endogenous reactant activity. Such treatment may involve the action of a clearing agent which chemically destroys the endogenous activity followed by treatment to inactivate the destructive action of such clearing agent.

For instance, reactant-degrading enzymes often appear naturally in biological fluids, particularly if the reactant is a coenzyme such as NAD, NADP, or ATP. There are many inhibitors of such coenzyme-degrading enzymes, for example, chelating agents which operate to deprive the enzymes of essential metal ion activators. As a specific example, NAP degrading enzymes are found in normal serum and have sufficient enzymatic activity to remove essentially all endogenous NAD activity from isolated serum within a few hours. The degrading activity of such enzymes may be effectively inhibited by addition of a chelating agent such as ethylenediamine tetraacetic acid. Elimination of the degrading activity may also be accomplished by adding a specific enzyme inhibitor. For example, ATP-degrading enzymes may be inhibited by addition of $\beta\gamma$ methylene ATP or $\alpha\beta$ methylene ATP.

The present invention will now be illustrated, but is not intended to be limited, by the following Examples.

EXAMPLE 1

Preparation of nicotinamide 6-(2-aminoethylamino) purine dinucleotide

Two (2) grams of nicotinamide adenine dinucleotide (NAD) were dissolved in 10 ml of water and 0.6 ml of ethyleneimine was added dropwise, the pH being maintained below 7 by the addition of 1 M perchloric acid. When addition of ethyleneimine was complete, the pH was adjusted to 4.5 and the reaction was incubated at 20°–25° C. At 24 hours intervals 0.6 ml of ethyleneimine was added and the pH readjusted to 4.5. After 96 hours, the solution was poured into 10 volumes of acetone at −10° C. The oil which formed was collected, washed with ether, and dissolved in approximately 50 ml of water in a flask.

The resulting solution was adjusted to pH 7.0–7.5 with 1 N sodium hydroxide, and 1 gram of sodium bicarbonate was added. Nitrogen was bubbled through the solution for from 4 to 5 minutes and 1 gram of sodium hydrosulfite was added. The flask was sealed tightly and allowed to stand at room temperature for 45 minutes. The solution was then oxygenated for 15 minutes and adjusted to pH 11.3 with sodium hydroxide. The solution was heated at 75° C. for 1 hour. Then the reaction mixture was cooled to room temperature and 0.6 grams of tris-(hydroxymethyl)-aminomethane was added, followed by 5 N hydrochloric acid to adjust the pH to 7.5. To the resulting solution was added 1000 International units of alcohol dehydrogenase and 1 ml of acetaldehyde. The decreasing optical density of the reaction mixture was monitored at 340 nm and when no further decrease was observed, the pH was adjusted to 3.5. The solution was poured into 10 volumes of acetone at −10° C. The oil which formed was separated and washed with ether, after which it was dissolved in 10 to 15 ml of water.

The resulting solution was introduced into a 2.5×90 cm column of Sephadex G-10, available from Pharmacia AB, Uppsala, Sweden, equilabrated with water. Fractions of 12 ml volume were collected. The wavelength of maximum optical absorption in the ultraviolet region and the optical density at such wavelength were determined for each fraction. Also, the optical density at 340 nm of each fraction after reduction with alcohol dehydrogenase was determined. The fractions which had an optical absorption maximum at 264 nm and had a ratio of optical density at 340 nm to that at 265 nm greater than 0.05 were pooled. The pooled material was concentrated to from 15 to 20 ml on a rotary evaporator and passed through a 2.5×28 cm column of Dowex 1-X8, available from Bio-Rad Laboratories, Richmond, Calif., equilabrated with water. Additional water was added to wash the pooled material through the column, and 10 ml fractions were collected. The fractions which had an optical density at 340 nm to that of 264 nm greater than 0.1 were pooled.

The pooled material was passed through a 5×45 cm column of Dowex 50-X2, available from Bio-Rad Laboratories, Richmond, Calif., equilabrated with water. Additional water was added to wash the pooled material through the column and 20 ml fractions were collected. The fractions which had an optical absorption maximum at 264 nm and had a ratio of optical density at 340 nm to that at 265 nm greater than 0.18 were pooled. The pooled material was concentrated to from 4 to 5 ml and purified by electrophoresis as follows.

The concentrated material was applied to a sheet of Whatman 3 MM paper, available from Reeve Angel, Clifton, N.J., in a 1 to 2 cm wide strip perpendicular to the direction of current flow. The paper was then wetted with 0.02 M sodium phosphate at pH 6.0. Electrophoresis was conducted according to the Durrum hanging paper method, as described in *Science* 121:829(1955), for 4–7 hours with a potential gradient of about 8.5 volts/cm. The location of the desired pyridine nucleotide derivative was determined by fluorescence developed after spraying a test strip of the paper with 0.5 M sodium cyanide according to the procedure described in *J. Biol. Chem.* 191:447(1951). The area containing the desired derivative was cut out of the paper and extracted with three (3) 50 ml volumes of water. The resulting extracts containing nicotinamide 6-(2-aminoethylamine) purine dinucleotide were pooled, concentrated to from 3 to 4 ml, and stored at −20° C.

EXAMPLE 2

Preparation of nicotinamide adenine dinucleotide-biotin conjugate

A 16 mg quantity of biotin was suspended in 1 ml of water containing 22 mg of nicotinamide 6-(2-aminoethylamino) purine dinucleotide prepared as in Example 1. A few drops of 0.1 N sodium hydroxide was added to aid dissolution of the biotin. A 240 mg quantity of 1-cyclohexyl-3-(2-morpholinoethyl)-carbodiimide metho-p-toluene sulfonate was added to the resulting solution and brought into solution by dropwise addition of 0.1 N hydrochloric acid. The reaction mixture was allowed to incubate at room temperature for 5 hours and was then poured into 10 ml of acetone at −10° C. The oil which formed was separated, washed twice with from 5 to 10 ml of ether and dissolved in from 1 to 2 ml of water. The resulting material was purified by electrophoresis on paper as in Example 1. Two fluorescent bands appeared after spraying with sodium cyanide, one having migrated toward the cathode and the other toward the anode. The latter band, which contained the NAD-biotin conjugate, was eluted with water and stored at −20° C.

EXAMPLE 3

Preparation of biotin-umbelliferone conjugate (2-Oxo-2-H-1-benzopyran-7-yl)-5-[cis-hexahydro-2-oxo-1H-thieno-(3,4-d-)-imidazole]valeric acid ester A solution of 300 mg (1.2 mmol) anhydrous biotin in 20 ml dry dimethylformamide was stirred at −10° C. under dry nitrogen gas and 0.17 ml (1.2 mmol)dry triethylamine was added. A solution of freshly distilled ethyl chloroformate (0.141 ml in 3 ml of dry ether) was added dropwise. After incubation for 30 min with stirring, the resulting precipitate was filtered under a dry nitrogen atmosphere and cooled immediately to −10° C. To the filtered residue was added a solution of 197 mg (1.2 mmol) anhydrous 7-hydroxycoumarin in 3 ml dry pyridine and stirred for 1 hour at −10° C. followed by 20 hours at 25° C. The solvents were evaporated under high vacuum at 40° C. After cooling, the resulting solid was filtered and recrystallized from methanol to yield the desired product (melting point=216°–218° C.). Calculated for $C_{19}H_{20}N_2P_5S$: C,48.75; H,4.19; N,7.21. Found: C,58.4; H,5.12; N,6,86.

EXAMPLE 4

Competitive binding-bioluminescence assay for biotin; effect of varying levels of biotin on the peak light intensity produced.

The bioluminescence reaction system used in this Example was based on the following reactions:

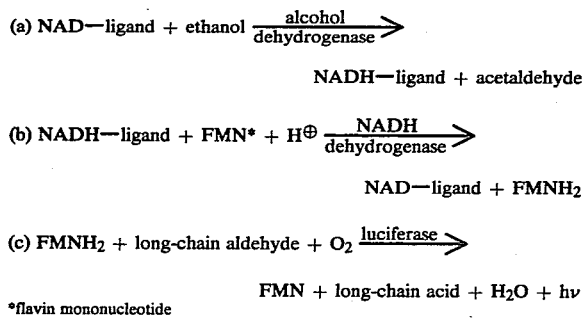

(a) NAD—ligand + ethanol $\xrightarrow{\text{alcohol dehydrogenase}}$ NADH—ligand + acetaldehyde (b) NADH—ligand + FMN* + H$^\oplus$ $\xrightarrow{\text{NADH dehydrogenase}}$ NAD—ligand + FMNH$_2$ (c) FMNH$_2$ + long-chain aldehyde + O$_2$ $\xrightarrow{\text{luciferase}}$ FMN + long-chain acid + H$_2$O + h$\nu$

*flavin mononucleotide

A. Preparation of light-generating solution

A light-generating solution for carrying out reactions (b) and (c) was prepared as follows. A reagent mixture was prepared containing 0.13 M phosphate buffer at pH 7.0, 0.67 wt% bovine serum albumin, 15.7 μM flavin mononucleotide (FMN), and 13.3 mM sodium acetate, and this mixture was stored in the dark at −20° C. An emulsion of 5 μl of dodecanal in 5 ml of water was prepared the day the light-generating solution was to be used. Lyophilized luciferase extracted from *Photobacterium fisheri* (enzyme available from Worthington Biochemical Corp., Freehold, N.J.) was added to 0.013 M phosphate buffer at pH 7.3 to a concentration of 20 mg/ml. After 30 minutes the resulting suspension was centrifuged at 1500 xg for 10 minutes and the pellet was discarded. The light generating solution was then prepared within 5 minutes of use by combining 75 μl of the reagent mixture, 5 μl of the dodecanal emulsion, and 20 μl of the luciferase solution.

B. Preparation of insolubilized binding partner

Avidin, which has a binding affinity for biotin, was insolubilized by being covalently bound to a water insoluble polymer bead as follows. A quantity of Sepharose 4B (available from Pharmacia AB, Uppsala, Sweden) was activated for bonding to avidin using the method of March et al, *Analytical Biochemistry* 60:149(1974). Approximately 4 ml of the activated Sepharose 4B was suspended in 8 ml of 0.1 M citrate buffer at pH 7.0. To the suspension was added 6 mg of avidin, having an activity of 9.9 units/mg, in 3 ml of water. One unit of avidin activity is that quantity of avidin capable of binding 1 μg of biotin. The resulting reaction mixture was stirred for 6 hours at 7° C. The avidin-bound-Sepharose 4B was then filtered, washed with 100 ml of 0.1 M sodium bicarbonate buffer at pH 9.0, and resuspended in 240 ml of 0.1 M tris-(hydroxymethyl)-aminomethane hydrochloride buffer at pH 8.0.

C. Control experiments

Nine specific binding reaction mixtures were prepared, each having a total volume of 0.19 ml and each containing 0.1 M tris-(hydroxymethyl)-aminomethane hydrochloride buffer at pH 8.0, 0.6 M ethanol, 0.01 M semicarbazide hydrochloride, and respectively the amounts of concentrations indicated in Table 1 of NAD, NAD-biotin conjugate, avidin-bound Sepharose 4B suspension (prepared according to Part B of this Example), and Sepharose 4B suspension (formed by suspending 1 ml of packed Sepharose 4B in 60 ml of 0.1 M tris-(hydroxymethyl)-aminomethane hydrochloride buffer at pH 8.0). The reaction mixtures were shaken gently for 15 minutes at room temperature. Then, 0.22 International units of alcohol dehydrogenase was added to each reaction mixture to initiate the reduction reaction. Semicarbazide combines with the acetaldehyde produced in reaction (a) to form a semicarbazone and thus to drive reaction (a) in the desired direction.

The reaction mixtures were shaken again for 15 minutes at room temperature. A 10 μl aliquot of the supernatant from each reaction mixture was then injected into a separate cuvette mounted in a DuPont Model 760 Bioluminescence Photometer (E. I. duPont de Nemours, Wilmington, Del.) containing 100 μl of the previously prepared light-generating solution which had been pre-incubated for from 2 to 3 minutes at 25° C. The results appear in Table 1.

TABLE 1

| reaction | concentration of NAD (nM) | concentration of NAD-biotin conjugate (nM) | avidin-bound Sepharose 4B suspension (μl) | Sepharose 4B suspension (μl) | peak light intensity |
|---|---|---|---|---|---|
| 1 | — | — | — | — | 1.2 |
| 2 | 21 | — | — | — | 159 |
| 3 | 21 | — | 20 | — | 147 |
| 4 | — | 10 | — | — | 45.9 |
| 5 | — | 21 | — | — | 110 |
| 6 | — | 21 | 20 | — | 28.5 |
| 7 | 21 | — | — | 10 | 154 |
| 8 | — | 21 | — | 10 | 114 |
| 9 | — | — | 20 | — | 1.6 |

The results of control reactions 1 and 9 show that in the absence of NAD and NAD-biotin conjugate very little light was produced. Reactions 2 and 3 yielded results indicating that the light producing reaction occurred when free NAD was added and that such reaction was substantially unaffected by the presence of avidin-bound-Sepharose 4B. The results of reactions 4, 5, and 6 show that the NAD-biotin conjugate was active in the light producing reaction, that the peak light intensity produced increased as more NAD-biotin conjugate was present, and that the presence of avidin-bound-Sepharose 4B inhibited light production. Comparison of the results of reactions 3 and 5 with those of 7 and 8 shows that the light producing reaction was not affected by the presence of plain Sepharose 4B.

D. Assay method

Five additional specific binding reaction mixtures were prepared, each having a volume of 0.19 ml and each containing 0.1 M tris-(hydroxymethyl)-aminomethane hydrochloride buffer at pH 8.0, 0.6 M ethanol, 0.01 M semicarbozide, and respectively the amounts or concentrations indicated in Table 2 of NAD-biotin conjugate, free biotin, and avidin-bound-Sepharose 4B suspension. Each reaction mixture was treated in the same manner as the control reaction mixtures in Part C of this Example. The results appear in Table 2.

TABLE 2

| reaction | concentration of NAD-biotin conjugate (nM) | concentration of biotin (nM) | avidin-bound Sepharose 4B suspension (μl) | peak light intensity |
|---|---|---|---|---|
| 10 | 21 | — | — | 79.1 |
| 11 | 21 | — | 20 | 17.4 |
| 12 | 21 | 79 | 20 | 43.1 |
| 13 | 21 | 158 | 20 | 59.9 |
| 14 | 21 | 158 | — | 79.7 |

The results of reactions 11, 12, and 13 show that free biotin and NAD-biotin conjugate compete effectively for the binding sites on the insolubilized avidin since the peak light intensity produced was dependent upon the amount of free biotin present. Reactions 10 and 14 gave results indicating that in the absence of insolubilized avidin, the peak light intensity produced was constant for vastly different concentrations of free biotin.

It was thus demonstrated in this Example that the amount of NAD-biotin conjugate in the liquid phase was inversely related to the amount of free biotin present and thus the assay method and means of the present invention are useful in the determination of a ligand in an unknown liquid sample.

EXAMPLE 5

Specific binding assays for avidin and biotin employing an enzyme substrate as labeling substance.

The specific binding assay systems used in this Example were based on the following reaction:

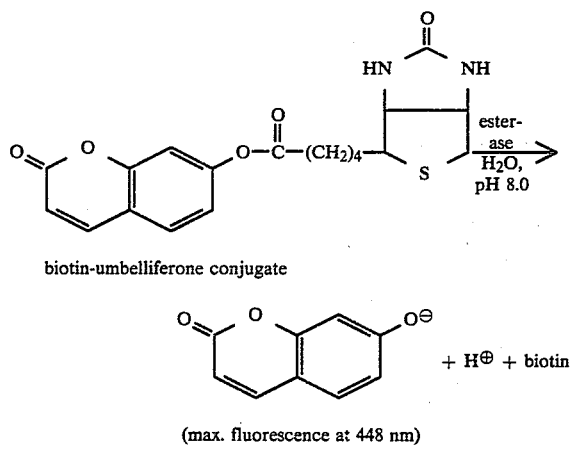

biotin-umbelliferone conjugate (max. fluorescence at 448 nm)

A. Preparation of insolubilized binding partner

Avidin was insolubilized by being covalently bound to a water insoluble polymer bead as in Part B of Example 4 except that after washing with 100 ml of 0.1 M sodium bicarbonate buffer at pH 9.0, the avidin-bound-Sepharose 4B was suspended in 12 ml of 0.1 M tris-(hydroxymethyl)-aminomethane hydrochloride buffer at pH 8.0 and diluted 1:1 with 0.1 M bis-hydroxyethylglycine hydrochloride buffer at pH 7.0.

B. Competitive binding assay for biotin; effect of various levels of biotin on the amount of umbelliferone liberated Eight specific binding reaction mixtures were prepared, each having a total volume of 0.2 ml and each containing 0.1 M bis-hydroxyethylglycine hydrochloride buffer at pH 7.0, 0.3 μM biotin-umbelliferone conjugate (prepared as in Example 3), 15 μl of the avidin-bound-Sepharose 4B suspension prepared as in Part A of this Example, and biotin in the concentration indicated in Table 3. The reaction mixtures were allowed to incubate at room temperature with gentle shaking for 20 minutes. Each reaction mixture was centrifuged and a 100 μl aliquot of the supernatant was combined with 2 ml of 0.1 M bis-hydroxyethylglycine hydrochloride buffer at pH 8.2 containing 1.08 units of porcine esterase. After a 5 minute incubation at room temperature, the fluorescence intensity produced in each reaction mixture at 448 nm with excitation at 364 nm was measured using an Amico-Bowman spectrophotofluometer. The results appear in Table 3.

TABLE 3

| reaction mixture | concentration of biotin (μM) | fluorescence intensity |
|---|---|---|
| 1 | 0.00 | 0.355 |
| 2 | 0.10 | 0.495 |
| 3 | 0.20 | 0.469 |
| 4 | 0.30 | 0.503 |
| 5 | 0.40 | 0.547 |
| 6 | 0.50 | 0.502 |
| 7 | 0.75 | 0.580 |
| 8 | 1.00 | 0.688 |

It was thus demonstrated in this Example that the amount of NAD-biotin in the liquid phase was directly proportional to the amount of free biotin present and thus the assay method and means of the present method are useful in the determination of a ligand in an unknown liquid sample.

What is claimed is:

1. In a heterogeneous specific binding assay method for determining a ligand in a liquid medium, which method comprises the steps of:
   (a) contacting said liquid medium with reagent means including a labeled conjugate comprising a specific binding substance coupled to a labeling substance, said reagent means and the ligand forming a binding reaction system producing a bound-phase and a free-phase of the labeled conjugate;
   (b) separating said bound-phase and said free-phase; and
   (c) determining said labeling substance in said bound-phase or said free-phase as a function of said ligand in said liquid medium, the improvement wherein said labeling substance is a chemiluminescent reactant and wherein said chemiluminescent label is determined in said bound-phase or said free-phase by forming the chemiluminescent reaction therein and measuring the light produced.

2. The method of claim 1 wherein the rate of said chemiluminescent reaction is measured as a function of said ligand in said medium.

3. The method of claim 1 wherein the light produced by said chemiluminescent reaction is measured as the total amount of light produced or a portion thereof.

4. The method of claim 1 wherein the light produced by said chemiluminescent reaction is measured as the peak intensity of light produced.

5. The method of claim 1 wherein said chemiluminescent label is luciferin, luminol, pyrogallol, or isoluminol.

6. The method of claim 1 wherein said chemiluminescent label is luminol or isoluminol, or a derivative thereof.

7. The method of claim 1 wherein said chemiluminescent reaction is enzymatic.

8. The method of claim 7 wherein said chemiluminescent label is a substrate for an enzyme involved in the enzymatic chemiluminescent reaction.

9. The method of claim 1 wherein said chemiluminescent reaction is non-enzymatic.

10. The method of claim 1 wherein said ligand is selected from the group consisting of antigens and antibodies thereto; haptens and antibodies thereto; and hormones, vitamins, metabolites, and pharmocological agents, and their receptors and binding substances.

11. The method of claim 1 wherein said liquid medium is a biological fluid.

12. A heterogeneous competitive binding assay method for determining a ligand in a liquid medium, comprising the steps of:
(a) contacting said liquid medium with (1) an insoluble form of one of said ligand or a specific binding partner thereof, and (2) a conjugate comprising the other of said ligand and binding partner labeled with a substance which is a reactant in a chemiluminescent reaction, to form a reaction mixture comprising a bound-phase and a free-phase of said labeled conjugate,
(b) separating said bound-phase and said free-phase,
(c) forming said chemiluminescent reaction in one of said bound-phase and said free-phase, and
(d) measuring the light produced as a function of said ligand in said liquid medium.

13. The method of claim 12 wherein said chemiluminescent label is luciferin, luminol, pyrogallol, or isoluminol.

14. The method of claim 12 wherein said chemiluminescent label is luminol or isoluminol, or a derivative thereof.

15. The method of claim 12 wherein said chemiluminescent reaction is enzymatic.

16. The method of claim 15 wherein said chemiluminescent label is a substrate for an enzyme involved in the enzymatic chemiluminescent reaction.

17. The method of claim 12 wherein said chemiluminescent reaction is non-enzymatic.

18. The method of claim 12 wherein said ligand is an antigen or hapten and said liquid medium is contacted with an insoluble form of an antibody thereto and with a chemiluminescent labeled form of said ligand.

19. A sandwich-type heterogeneous specific binding assay method for determining a ligand in a liquid medium, which method comprises the steps of:
(a) contacting said liquid medium with (1) an insoluble form of a specific binding partner to said ligand, and (2) a labeled conjugate comprising a specific binding partner to said ligand labeled with a substance which is a reactant in a chemiluminescent reaction, to form a bound-phase comprising said labeled conjugate bound to ligand bound to said insoluble binding partner and a free-phase comprising said labeled conjugate not so bound,
(b) separating said bound-phase and said free-phase,
(c) forming said chemiluminescent reaction is one of said separated phases, and
(d) measuring the light produced as a function of the ligand in the medium under assay.

20. The method of claim 19 wherein steps (a) and (b) are accomplished by:
(i) first contacting said liquid medium with said insoluble binding partner, to form a reaction mixture comprising, as a first bound-phase, ligand from said medium bound to said insoluble binding partner,
(ii) separating said first-bound phase from the reaction mixture,
(iii) then contacting said separated first bound-phase with said chemiluminescent labeled conjugate to form a second bound-phase comprising said labeled conjugate bound to said first bound-phase and a free-phase comprising said labeled conjugate not so bound, and
(iv) separating said second bound-phase and said free-phase.

21. The method of claim 19 wherein said specific binding partner in said labeled conjugate is the same as that in said insoluble form.

22. The method of claim 19 wherein said chemiluminescent label is luciferin, luminol, pyrogallol, or isoluminol.

23. The method of claim 19 wherein said chemiluminescent label is luminol or isoluminol, or a derivative thereof.

24. The method of claim 19 wherein said chemiluminescent reacton is enzymatic.

25. The method of claim 24 wherein said chemiluminescent label is a substrate for an enzyme involved in the enzymatic chemiluminescent reaction.

26. The method of claim 19 wherein said chemiluminescent reaction is non-enzymatic.

27. The method of claim 19 wherein said ligand is an antigen and wherein said insoluble form of a specific binding partner thereof is an insoluble form of an antibody thereto and said labeled conjugate is a chemiluminescent labeled form of an antibody thereto.

28. A heterogeneous method of determining the presence of a ligand in a medium suspected of containing said ligand which comprises: bringing together in an aqueous liquid zone: (1) said medium; (2) a chemiluminescent labeled ligand; and (3) a binding partner having sites capable of bonding to said ligand and said chemiluminescent labeled ligand; the concentration of said binding partner being such that there are insufficient binding sites to combine with all of said labeled ligand present in the three component mixture; and analyzing in said zone for the effect of said medium on the amount of chemiluminescent labeled ligand bound to said binding partner by physically separating free chemiluminescent labeled ligand from chemiluminescent labeled ligand bound to said binding partner and measuring chemiluminescence in either of the separated free and bound phases.

29. A method according to claim 28 wherein said ligand is insulin.

30. A method according to claim 28 wherein said chemiluminescent labeled ligand is an insulin-luminol conjugate.

31. A method according to claim 28 wherein said ligand is digoxin.

32. A method according to claim 31 wherein said chemiluminescent labeled ligand is a digoxin-luminol conjugate.

33. A method according to claim 28 wherein said binding partner is an antibody.

34. A method according to claim 28 wherein said ligand is a drug, its analog or metabolite.

35. A method according to claim 34 wherein said drug is selected from the group consisting of morphine, barbiturates, diphenylhydantoin, and metabolites and analogs thereof.

36. A method according to claim 28 wherein said ligand is a protein.

37. A method according to claim 36 wherein said protein is selected from the group consisting of polypeptides, antibodies, hormones, insulin, chorionic gondotropin, bradykinin, and thyroid binding globulin.

38. A method according to claim 28 wherein said ligand is a steroid.

39. A method according to claim 28 wherein said ligand is a vitamin.

40. The method of claim 28 wherein said binding partner is isolated and the amount of chemiluminescent ligand bound thereto is determined by adding an activator and measuring the light emitted.

41. The method of claim 28 wherein said chemiluminescent ligand is a conjugate of a ligand with a chemiluminescent substance selected from the group consisting of luciferin and luminol.

42. Reagent means for use in a heterogeneous competitive binding assay for determining a ligand in a liquid medium, comprising (a) an insoluble form of one of said ligand or a specific binding partner thereof, and (b) a conjugate comprising the other of said ligand and binding partner labeled with a substance which is a reactant in a chemiluminescent reaction.

43. The reagent means of claim 42 wherein said chemiluminescent label is luciferin, luminol, pyrogallol, or isoluminol.

44. The reagent means of claim 42 wherein said chemiluminescent label is luminol or isoluminol, or a derivative thereof.

45. The reagent means of claim 42 wherein said chemiluminescent reaction is enzymatic.

46. The reagent means of claim 45 wherein said chemiluminescent label is a substrate for an enzyme involved in the enzymatic chemiluminescent reaction.

47. The reagent means of claim 42 wherein said chemiluminescent reaction is non-enzymatic.

48. The reagent means of claim 42 wherein said ligand is an antigen or hapten and wherein said means comprises an insoluble form of an antibody thereto and a chemiluminescent labeled form of said ligand.

49. Reagent means for use in a sandwich-type heterogeneous binding assay for determining a ligand in a liquid medium, comprising (a) an insoluble form of a specific binding partner of said ligand, and (b) a conjugate comprising a specific binding partner of said ligand labeled with a substance which is a reactant in a chemiluminescent reaction.

50. The reagent means of claim 49 wherein said specific binding partner in said labeled conjugate is the same as that in said insoluble form.

51. The reagent means of claim 49 wherein said chemiluminescent label is luciferin, luminol, pyrogallol, or isoluminol.

52. The reagent means of claim 49 wherein said chemiluminescent label is luminol or isoluminol, or a derivative thereof.

53. The reagent means of claim 49 wherein said chemiluminescent reaction is enzymatic.

54. The reagent means of claim 53 wherein said chemiluminescent label is a substrate for an enzyme involved in the enzymatic chemiluminescent reaction.

55. The reagent means of claim 49 wherein said chemiluminescent reaction is non-enzymatic.

56. The reagent means of claim 49 wherein said ligand is an antigen and wherein said insoluble form of a specific binding partner thereof is an insoluble form of an antibody thereto and said labeled conjugate is a chemiluminescent labeled form of an antibody thereto.

* * * * *

UNITED STATES PATENT AND TRADEMARK OFFICE
Certificate

Patent No. 4,380,580            Patented Apr. 19, 1983

Robert C. Boguslaski, Robert J. Carrico and James E. Christner

Application having been made by Robert C. Boguslaski, Robert J. Carrico and James E. Christner, the inventors named in the patent above identified, and Miles Laboratories, Inc. the assignees, for the issuance of a certificate under the provisions of Title 35, Section 256, of the United States Code, deleting the name of James E. Christner as a joint inventor, and a showing and proof of facts satisfying the requirements of the said section having beem submitted, it is this 8th day of May, 1984, certified that the name of the said James E. Christner is hereby deleted from the said patent as a joint inventor with the said Robert C. Boguslaski and Robert J. Carrico.

Fred W. Sherling,
*Associate Solicitor.*